(12) United States Patent
Kesten et al.

(10) Patent No.: US 10,362,965 B2
(45) Date of Patent: Jul. 30, 2019

(54) SYSTEM AND METHOD TO MAP STRUCTURES OF NASAL CAVITY

(71) Applicant: Acclarent, Inc., Menlo Park, CA (US)

(72) Inventors: Randy J. Kesten, Mountain View, CA (US); Arthur M. Lin, Fremont, CA (US); Thomas R. Jenkins, Alameda, CA (US); Rohit Girotra, Mountain View, CA (US); Sandra W. Ruggles, Sunnyvale, CA (US); Meera L. Sankaran, Cupertino, CA (US); Kathryn Olson, San Diego, CA (US)

(73) Assignee: Acclarent, Inc., Irvine, CA (US)

( * ) Notice: Subject to any disclaimer, the term of this patent is extended or adjusted under 35 U.S.C. 154(b) by 451 days.

(21) Appl. No.: 14/825,551

(22) Filed: Aug. 13, 2015

(65) Prior Publication Data
US 2016/0310042 A1 Oct. 27, 2016

Related U.S. Application Data

(60) Provisional application No. 62/150,912, filed on Apr. 22, 2015.

(51) Int. Cl.
*A61B 5/00* (2006.01)
*A61B 5/06* (2006.01)
(Continued)

(52) U.S. Cl.
CPC .............. *A61B 5/066* (2013.01); *A61B 5/055* (2013.01); *A61B 5/6851* (2013.01);
(Continued)

(58) Field of Classification Search
None
See application file for complete search history.

(56) References Cited

U.S. PATENT DOCUMENTS 4,509,945 A 4/1985 Kramann et al.
5,810,835 A * 9/1998 Ryan ................. A61M 25/0084
604/159

(Continued)

FOREIGN PATENT DOCUMENTS

WO WO 2006/062996 A2 6/2006
WO WO 2011/140535 A1 11/2011
WO WO 2011140535 A1 * 11/2011 ............. A61B 17/24

OTHER PUBLICATIONS

F. J. Canny, "A Computational Approach to Edge Detection," IEEE Trans PAMI, 8(6):679-698, Nov. 1986, 20 pgs.
(Continued)

*Primary Examiner* — Tse W Chen
*Assistant Examiner* — Joanne M Hoffman
(74) *Attorney, Agent, or Firm* — Frost Brown Todd LLC

(57) ABSTRACT

An apparatus includes a handle assembly, a guide tube, and a wire. The handle assembly includes a body and an actuator. The guide tube extends distally from the handle assembly and includes a distal end. The wire is slidably disposed in the guide tube. The wire has a distal end including a sensor. The sensor is configured to cooperate with a navigation system to generate a map of anatomical structures within a patient. The wire is coupled with the actuator. The actuator is movable relative to the body to move the wire relative to the guide tube.

20 Claims, 25 Drawing Sheets

(51) Int. Cl.
  *A61B 17/24*   (2006.01)
  *A61B 17/34*   (2006.01)
  *A61B 34/20*   (2016.01)
  *A61B 5/055*   (2006.01)
  *A61B 8/08*    (2006.01)
  *A61B 17/00*   (2006.01)
  *A61B 90/00*   (2016.01)

(52) U.S. Cl.
  CPC ............ *A61B 8/0841* (2013.01); *A61B 17/24* (2013.01); *A61B 17/3421* (2013.01); *A61B 34/20* (2016.02); *A61B 17/3415* (2013.01); *A61B 2017/0046* (2013.01); *A61B 2017/00367* (2013.01); *A61B 2017/00946* (2013.01); *A61B 2034/2051* (2016.02); *A61B 2090/0811* (2016.02); *A61B 2217/005* (2013.01)

(56) References Cited

U.S. PATENT DOCUMENTS

| | | | |
|---|---|---|---|
| 6,685,722 B1 * | 2/2004 | Rosenbluth | A61B 17/22032 606/159 |
| 6,929,624 B1 * | 8/2005 | Del Castillo | A61M 25/0631 604/164.07 |
| 7,720,521 B2 | 5/2010 | Chang et al. | |
| 8,123,722 B2 | 2/2012 | Chang et al. | |
| 8,137,285 B1 * | 3/2012 | Regan | A61B 5/4893 600/554 |
| 8,190,389 B2 | 5/2012 | Kim et al. | |
| 8,320,711 B2 | 11/2012 | Altmann et al. | |
| 8,702,626 B1 | 4/2014 | Kim et al. | |
| 8,979,888 B2 | 3/2015 | Morriss et al. | |
| 9,167,961 B2 | 10/2015 | Makower et al. | |
| 9,198,736 B2 | 12/2015 | Kim et al. | |
| 9,623,213 B2 | 4/2017 | Kesten et al. | |
| 9,839,481 B2 * | 12/2017 | Blumenkranz | A61B 17/2909 |
| 2002/0087169 A1 * | 7/2002 | Brock | A61B 17/0469 606/139 |
| 2002/0107530 A1 * | 8/2002 | Sauer | A61B 1/0014 606/139 |
| 2002/0143319 A1 * | 10/2002 | Brock | A61B 5/0086 606/1 |
| 2003/0088187 A1 * | 5/2003 | Saadat | A61B 5/015 600/547 |
| 2004/0034369 A1 * | 2/2004 | Sauer | A61B 1/00071 606/139 |
| 2005/0143770 A1 * | 6/2005 | Carter | A61B 1/018 606/170 |
| 2005/0197623 A1 * | 9/2005 | Leeflang | A61M 25/0144 604/95.04 |
| 2005/0272975 A1 * | 12/2005 | McWeeney | A61B 1/00071 600/113 |
| 2006/0064101 A1 * | 3/2006 | Arramon | A61B 17/32002 606/82 |
| 2006/0095022 A1 * | 5/2006 | Moll | A61B 8/12 606/1 |
| 2007/0156225 A1 * | 7/2007 | George | A61F 2/95 623/1.12 |
| 2007/0167682 A1 * | 7/2007 | Goldfarb | A61B 1/00135 600/114 |
| 2007/0208252 A1 | 9/2007 | Makower | |
| 2007/0249896 A1 * | 10/2007 | Goldfarb | A61B 1/0014 600/101 |
| 2008/0228135 A1 * | 9/2008 | Snoderly | A61B 17/1671 604/95.04 |
| 2009/0005754 A1 * | 1/2009 | Soetermans | A61M 25/0169 604/500 |
| 2009/0062871 A1 * | 3/2009 | Chin | A61B 1/00082 606/86 R |
| 2009/0080738 A1 | 3/2009 | Zur et al. | |
| 2009/0187098 A1 * | 7/2009 | Makower | A61B 5/411 600/424 |
| 2010/0094310 A1 * | 4/2010 | Warring | A61M 25/0606 606/108 |
| 2010/0274188 A1 * | 10/2010 | Chang | A61B 1/227 604/96.01 |
| 2011/0060214 A1 | 3/2011 | Makower | |
| 2011/0112551 A1 * | 5/2011 | Adams | A61B 17/122 606/142 |
| 2012/0029495 A1 * | 2/2012 | Wittenberger | A61B 18/02 606/21 |
| 2012/0046652 A1 * | 2/2012 | Sokel | A61F 2/95 606/1 |
| 2012/0071856 A1 * | 3/2012 | Goldfarb | A61B 17/24 604/514 |
| 2012/0071857 A1 * | 3/2012 | Goldfarb | A61B 17/24 604/514 |
| 2012/0123257 A1 * | 5/2012 | Stokes, Jr. | A61M 5/007 600/432 |
| 2012/0136207 A1 * | 5/2012 | Goldfarb | A61B 1/00126 600/106 |
| 2013/0066358 A1 * | 3/2013 | Nalluri | A61F 11/002 606/199 |
| 2014/0018732 A1 * | 1/2014 | Bagaoisan | A61M 25/0136 604/95.04 |
| 2014/0066901 A1 * | 3/2014 | Dinger, III | A61M 25/0105 604/514 |
| 2014/0200444 A1 | 7/2014 | Kim et al. | |
| 2014/0364725 A1 | 12/2014 | Makower | |
| 2017/0172586 A1 * | 6/2017 | Wallace | A61B 17/1671 |
| 2018/0092633 A1 * | 4/2018 | Peliks | A61B 10/0266 |

OTHER PUBLICATIONS

International Search Report and Written Opinion dated Jul. 13, 2016 for Application No. PCT/US2016/026910, 13 pgs.
U.S. Appl. No. 62/150,912, filed Apr. 22, 2015.
U.S. Appl. No. 62/150,954, filed Apr. 22, 2015.
European Examination Report dated Apr. 9, 2019 for Application No. 16721294.3, 5 pages.

* cited by examiner

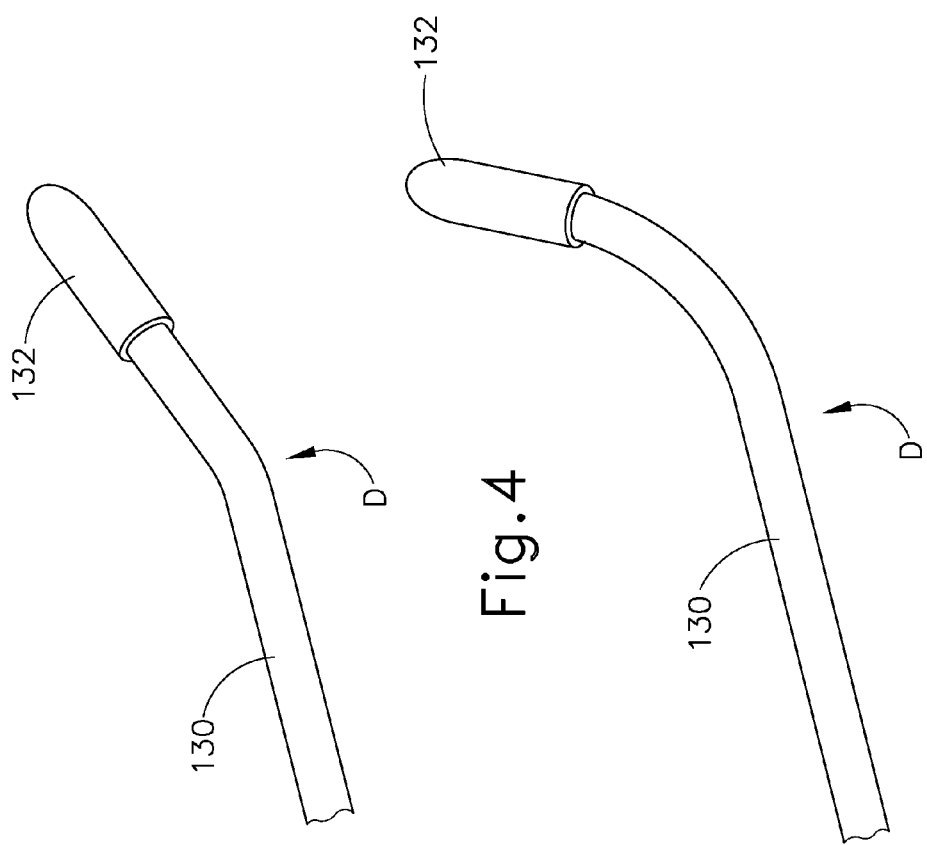

SYSTEM AND METHOD TO MAP STRUCTURES OF NASAL CAVITY

PRIORITY

This application claims priority to U.S. Provisional Patent App. No. 62/150,912, entitled "System and Method to Map Structures of Nasal Cavity," filed Apr. 22, 2015, the disclosure of which is incorporated by reference herein.

BACKGROUND

Image-guided surgery (IGS) is a technique wherein a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Diamond Bar, Calif.; systems available from Surgical Navigation Technologies, Inc., of Louisville, Colo.; and systems available from Calypso Medical Technologies, Inc., of Seattle, Wash.

Still other examples of methods, devices, and/or systems that may be modified for use in accordance with the teachings herein include but are not limited to those disclosed in U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Still further examples of methods, devices, and/or systems that may be modified for use in accordance with the teachings herein include but are not limited to those disclosed in U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. Pub. No. 2012/0245456, entitled "Adapter for Attaching Electromagnetic Image Guidance Components to a Medical Device," published Sep. 27, 2012, issued as U.S. Pat. No. 9,198,736 on Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. Pub. No. 2008/0281156, entitled "Methods and Apparatus for Treating Disorders of the Ear Nose and Throat," published Nov. 13, 2008, issued as U.S. Pat. No. 9,167,961 on Oct. 27, 2015, the disclosure of which is incorporated by reference herein; and U.S. Pat. Pub. No. 2007/0208252, entitled "Systems and Methods for Performing Image Guided Procedures Within the Ear, Nose, Throat and Paranasal Sinuses," published Sep. 6, 2007, now abandoned, the disclosure of which is incorporated by reference herein.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2 dimensional, line-of-sight view. The use of image guidance systems provides a real time, 3 dimensional view of all of the anatomy surrounding the operative field, not just that which is actually visible in the spatially limited, 2 dimensional, direct line-of-sight endoscopic view. As a result, image guidance systems may be particularly useful during performance of FESS, balloon sinuplasty, and/or other ENT procedures, especially in cases where normal anatomical landmarks are not present or are difficult to visualize endoscopically.

There remains a need in the art for the development of improved sensor equipped instruments and devices for use in image guided ENT procedures. While several systems and methods have been made and used to provide image guidance in medical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 4 depicts a perspective view of a distal end of another exemplary flexible wire that may be incorporated into the cartridge of FIG. 2;

FIG. 5 depicts a perspective view of a distal end of yet another exemplary flexible wire that may be incorporated into the cartridge of FIG. 2;

Figure 1:
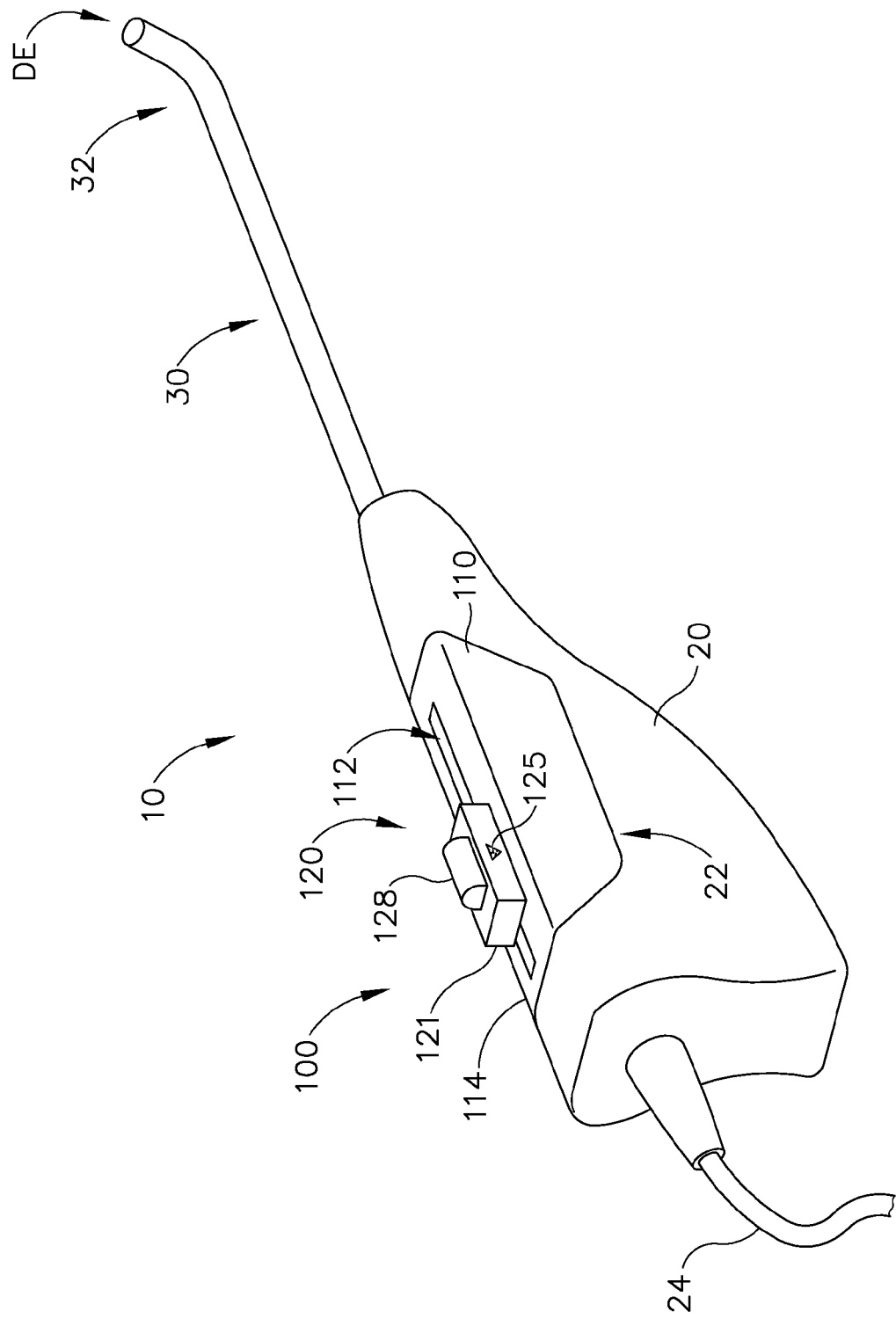
FIG. 1 depicts a perspective view of an exemplary mapping and navigation device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY MAPPING AND NAVIGATIONAL DEVICE

FIG. 1 shows an exemplary mapping and navigational device (10) that may be used to map and/or navigate the nasal cavity of a patient, passageways associated with the nasal cavity of a patient (e.g., paranasal sinus ostia and cavities, the frontal recess, the Eustachian tube, etc.), and/or other anatomical passageways (e.g., within the ear, nose, or throat, etc.). Mapping and navigational device (10) of the present example comprises a handle (20), a guide tube (30), and a cartridge assembly (100). In the present example, handle (20) is formed of stainless steel, though it should be understood that any other suitable material(s) may be used. In some instances, the combination of handle (20) and guide tube (30) is provided as a reusable device (e.g., multi-patient, sterilizable); while cartridge assembly (100) is provided as a disposable device (e.g., single patient only, non-sterilizable). Handle (20) of the present example may be grasped like a pencil by a user. Alternatively, various other suitable configurations and gripping techniques may be used, including but not limited to a pistol grip configuration or a power grip technique. Guide tube (30) extends distally from handle (20).

All or a portion (e.g., between 0.3 cm and 2 inches) of guide tube (30) may comprise a material having a low magnetic permeability, including by not limited to 316 stainless steel, nitinol, cobalt chromium, tungsten, PEEK, and polycarbonate, such that guide tube (30) will not interfere with any signals from wire (130). In some versions, only the distal portion of guide tube (30) is non-ferromagnetic or otherwise has low magnetic permeability. Guide tube (30) of the present example includes a bent distal portion (32) at its distal end (DE). In some versions, guide tube (30) is configured similar to the Relieva Flex™ Sinus Guide Catheter by Acclarent, Inc. of Menlo Park, Calif. By way of example only, bent distal portion (32) may provide a bend angle of approximately 20°. Alternatively, any other suitable bend angle may be used. In the present example, guide tube (30) is rigid. In some other versions, guide tube (30) is malleable such that the operator may deform guide tube (30) to any desired bend angle and guide tube (30) may maintain the selected bend angle during subsequent use. Other suitable forms that guide tube (30) may take will be apparent to those of ordinary skill in the art in view of the teachings herein.

Figure 2:
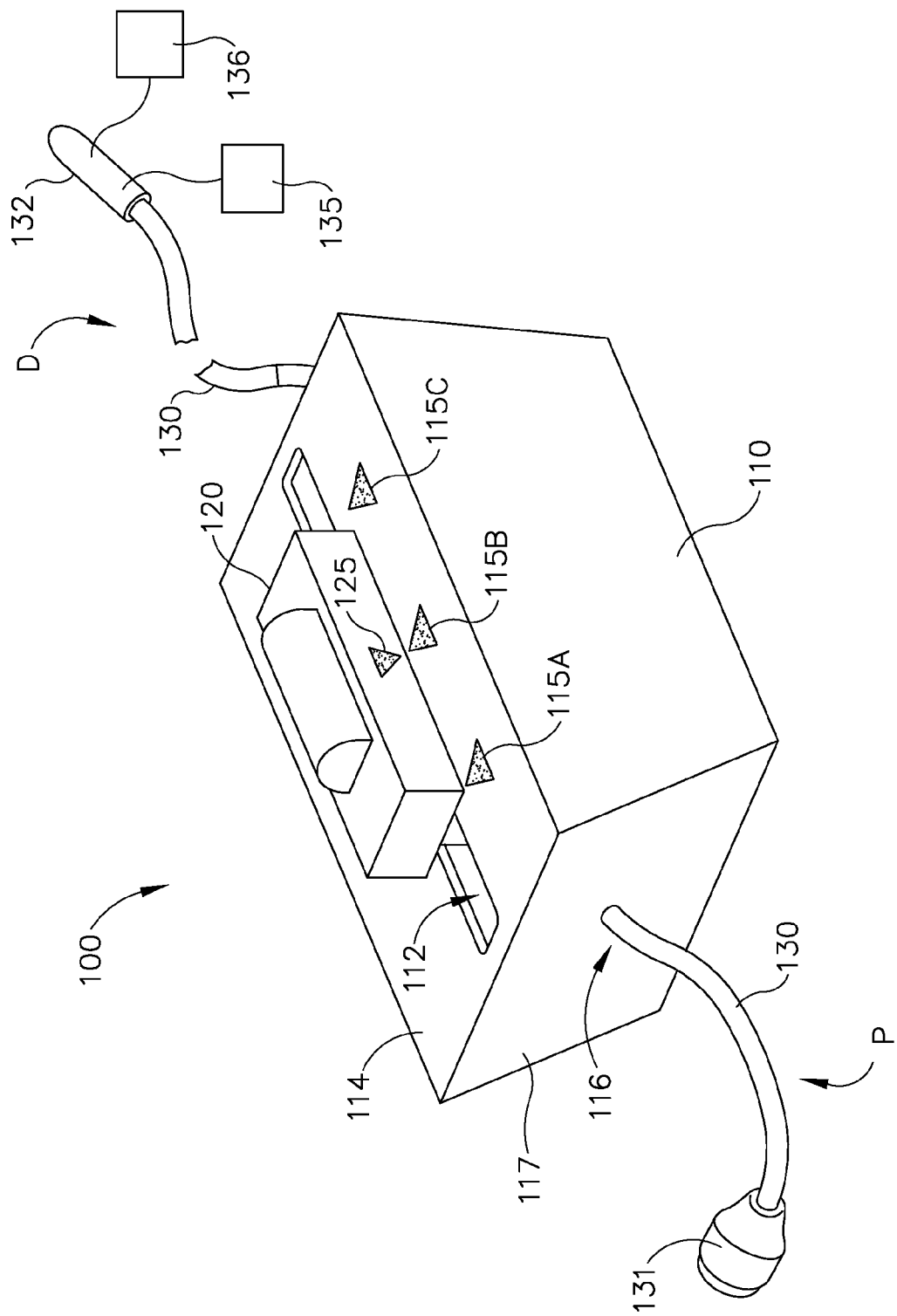
FIG. 2 depicts a perspective view of an exemplary single-use cartridge of the device of FIG. 1.

FIG. 2 shows cartridge assembly (100). As will be described in more detail below, cartridge assembly (100) is configured for receipt in an opening (22) of handle (20) to thereby couple with handle (20). In some alternative versions, the features and functionality of cartridge assembly (100) are fully integrated into handle (20). Cartridge assembly (100) comprises a housing (110), a manual actuator (120), and a flexible wire (130). Housing (110) includes a longitudinal slot (112) formed in a top surface (114) of housing (110). A sled (121) of actuator (120) is slidably disposed within slot (112) of housing (110) via a pair of longitudinal channels (123) (FIG. 3) formed in opposing sides of sled (121) such that, as will be described in more detail below, actuator (120) is configured to translate within slot (112) between a proximal longitudinal position (FIG. 6C), an intermediate longitudinal position (FIG. 6D), and a distal longitudinal position (FIG. 6E). Top surface (114) of housing (110) includes a series of visible markers (115A, 115B 115C) positioned adjacent slot (112). Markers (115A, 115B 115C) correspond to the proximal longitudinal position, the intermediate longitudinal position, and the distal longitudinal position of actuator (120), respectively. Actuator (120) includes a visible marker (125) that is configured to align with markers (115A, 115B 115C) of housing (110) to visually indicate that actuator (120) has reached each corresponding longitudinal position. Additionally or alternatively, housing (110) and/or actuator (120) may further include features (e.g. mechanical detents) that are configured to provide tactile and/or audible feedback to the operator as actuator (120) reaches each longitudinal position.

Wire (130) of the present example comprises a flexible stacked-coil design. Wire (130) extends completely through housing (110) such that a proximal portion (P) of wire (130) extends proximally from housing (110) and such that a distal portion (D) of wire (130) extends distally from housing (110). Proximal portion (P) of wire (130) is fixedly secured within an opening (116) formed in a proximal surface (117) of housing (110) such that proximal portion (P) is configured to remain stationary relative to housing (110). Various suitable structures and techniques that may be used to fixedly secure proximal portion (P) of wire (130) in opening (116) will be apparent to those of ordinary skill in the art in view of the teachings herein. As will be described in more detail below, proximal portion (P) includes an adapter (131). Adapter (131) is configured to couple wire (130) of cartridge assembly (100) with a cable (24) of handle (20). In some versions, adapter (131) is replaced with one or more pins, one or more exposed electrical contacts, one or more sockets, and/or one or more other features that are configured to mate with complementary features in handle (20) when cartridge assembly (100) is coupled with handle (20). These alternative mating features of cartridge assembly (100) and handle (20) may provide electrical communication between wire (130) and cable (24) when cartridge assembly (100) is coupled with handle (20). Various suitable forms that such mating features may take will be apparent to those of ordinary skill in the art in view of the teachings herein.

A strain relief (28) is provided at the point where cable (24) exits handle (20). Cable (24) may be coupled with a console (210) as will be described in greater detail below. Also as will be described in more detail below, distal portion (D) of wire (130) is slidably disposed within an opening (not shown) formed in a distal surface (not shown) of housing (110) such that distal portion (D) is configured to translate relative to housing (110). Wire (130) includes a service loop (S) disposed between proximal portion (P) and distal portion (D). Service loop (S) is positioned within housing (110) and is configured to provide freedom of movement to distal portion (D) so as to accommodate translation of distal portion (D) relative to housing (110) while proximal portion (P) remains fixed relative to housing (110).

Figure 3:
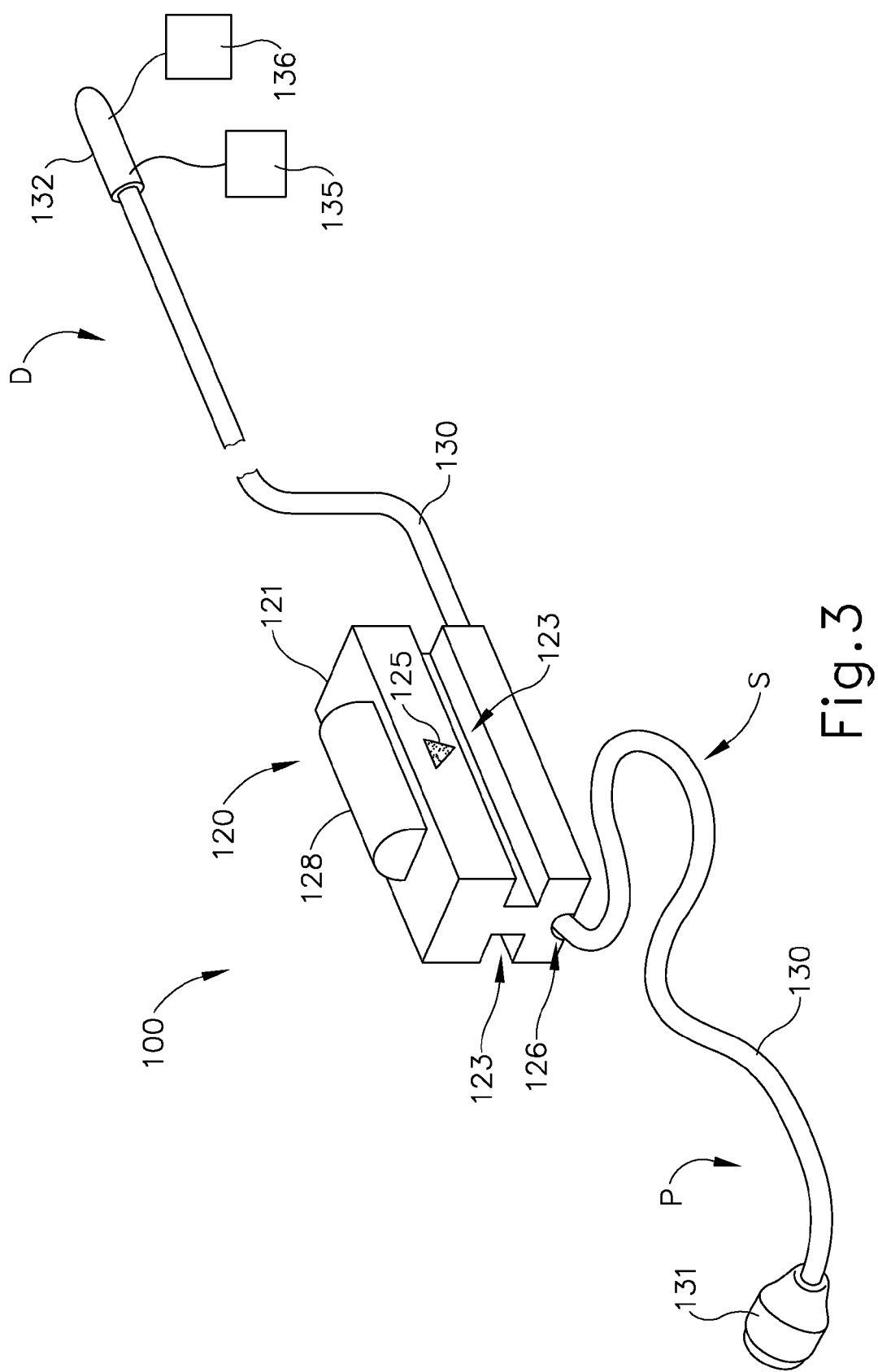
FIG. 3 depicts a perspective view of an exemplary flexible wire and actuator of the cartridge of FIG. 2.

As best seen in FIG. 3, wire (130) is positioned within a longitudinal channel (126) formed in a bottom surface of sled (121) of actuator (120). Wire (130) is secured within channel (126) such that translation of actuator (120) within slot (112) of housing (110) causes concurrent translation of wire (130). In particular, actuator (120) is coupled with distal portion (D) of wire (130), distally of service loop (S), such that translation of actuator (120) within slot (112) causes concurrent translation of distal portion (D) of wire (130). As mentioned above, service loop (S) is configured to provide freedom of movement to distal portion (D) so as to accommodate translation of distal portion (D) relative to housing (110) while proximal portion (P) remains fixed relative to housing (110).

As will be described in more detail below, with cartridge assembly (100) coupled within handle (20), distal portion (D) of wire (130) is configured to be slidably received within a bore (26) of handle (20) and within guide tube (30) such that wire (130) is configured to translate within bore (26) and guide tube (30) in response to translation of actuator (120) relative to housing (110). This translation of wire (130) causes translation of a distal end (132) of wire (130) relative to guide tube (30) as actuator (120) translates between the proximal longitudinal position, the intermediate longitudinal position, and the distal longitudinal position as described above and as will be described in more detail below. Guide tube (30) defines a lumen that is configured to slidably receive wire (130), such that guide tube (30) may guide wire (130) out through bent distal end (32). In some versions of cartridge assembly (100), guide tube (30) may be an integral component of cartridge assembly (100).

Actuator (120) of the present example further comprises a rotatable member (128) rotatably disposed within an upper portion of sled (121). Rotatable member (128) of the present example is rotatable within and relative to sled (121). A portion of rotatable member (128) is exposed relative to sled (121) such that the operator may directly engage rotatable member (128) with a finger or thumb to thereby cause rotation of rotatable member (128). Rotatable member (128) is mechanically coupled with wire (130) such that rotation of rotatable member (128) about the longitudinal axis of rotatable member (128) causes concurrent rotation of wire (130) about the longitudinal axis of wire (130). In particular, rotatable member (128) may be mechanically associated with the portion of wire (130) that is secured within channel (126) of sled (121) such that rotation of rotatable member (128) is configured to cause concurrent rotation of wire (130). By way of example only, rotatable member (128) and wire (130) may be coupled via gears, one or more cables, one or more belts, and/or any other components that are operable to provide rotation of wire (130) in response to rotation of rotatable member (128). Wire (130) has sufficient strength against torsion such that rotation of wire (130) by rotatable member (128) is communicated to distal end (132) of wire (130). In some alternative versions, rotatable member (128) is omitted.

As shown in FIG. 3, distal end (132) of wire (130) of the present example is substantially straight and includes an atraumatic distal tip. As shown in FIGS. 4 and 5, the distal end of wire (130) may include a preformed bend (FIG. 4), a preformed curve (FIG. 5), or any other appropriate configuration. It should therefore be appreciated that rotation of wire (130) may result in realignment or reorientation of distal end (132). It should also be understood that the tip of distal end (132) may have any suitable configuration, including but not limited to a dome shape, a ball shape, a blueberry shape, or any other suitable shape.

As shown schematically in FIGS. 2-3 and 6A-6E, distal end (132) of wire (130) of the present example comprises a position sensor (135) and an ultrasound sensor (136). As will be described in more detail below, sensors (135, 136) enable distal end (132) of wire (130) to be used to provide mapping and/or navigation of the nasal cavity of a patient, passageways associated with the nasal cavity of a patient (e.g., paranasal sinus ostia and cavities, the frontal recess, the Eustachian tube, etc.), and/or other anatomical passageways (e.g., within the ear, nose, or throat, etc.). It should be understood that some variations of wire (130) may include position sensor (135) and omit ultrasound sensor (136). Some other variations of wire (130) may include ultrasound sensor (136) and omit position sensor (135). In addition to or in lieu of having position sensor (135) and/or ultrasound sensor (136), distal end (132) of wire (130) may include a camera that is configured to provide real-time visualization of a surgical field.

In the present example, position sensor (135) includes a coil that is embedded within distal end (132) of wire (130) and that is in communication with one or more electrical conduits that extend along the length of wire (130). When position sensor (135) is positioned within an electromagnetic field, movement of position sensor (135) within that magnetic field may generate electrical current in the coil, and this electrical current may be communicated along wire (132) and further along cable (24). This phenomenon may enable a system (200) to determine the location of distal end (132) within a three dimensional space as will be described in greater detail below.

By way of example only, position sensor (135) and/or other components of wire (130) may be constructed and operable in accordance with at least some of the teachings of U.S. Pat. No. 8,702,626, the disclosure of which is incorporated by reference herein; U.S. Pat. No. 8,320,711, the disclosure of which is incorporated by reference herein; U.S. Pat. No. 8,190,389, the disclosure of which is incorporated by reference herein; U.S. Pat. No. 8,123,722, the disclosure of which is incorporated by reference herein; U.S. Pat. No. 7,720,521, the disclosure of which is incorporated by reference herein; U.S. Pat. Pub. No. 2014/0364725, now abandoned, the disclosure of which is incorporated by reference herein; U.S. Pat. Pub. No. 2014/0200444, now abandoned, the disclosure of which is incorporated by reference herein; U.S. Pat. Pub. No. 2012/0245456, issued as U.S. Pat. No. 9,198,736 on Dec. 1, 2015, the disclosure of which is incorporated by reference herein; U.S. Pat. Pub. No. 2011/0060214, now abandoned, the disclosure of which is incorporated by reference herein; U.S. Pat. Pub. No. 2008/0281156, issued as U.S. Pat. No. 9,167,961 on Oct. 27, 2015, the disclosure of which is incorporated by reference herein; and/or U.S. Pat. Pub. No. 2007/0208252, now abandoned, the disclosure of which is incorporated by reference herein. As another merely illustrative example, wire (130) may be constructed and operable in accordance with at least some of the teachings of U.S. Provisional Pat. App. No. 62/150,954, entitled "Guidewire with Navigation Sensor," filed on Apr. 22, 2015, the disclosure of which is incorporated by reference herein. Other suitable ways in which wire (130) may be constructed and operable will be apparent to those of ordinary skill in the art in view of the teachings herein.

Figure 6A:
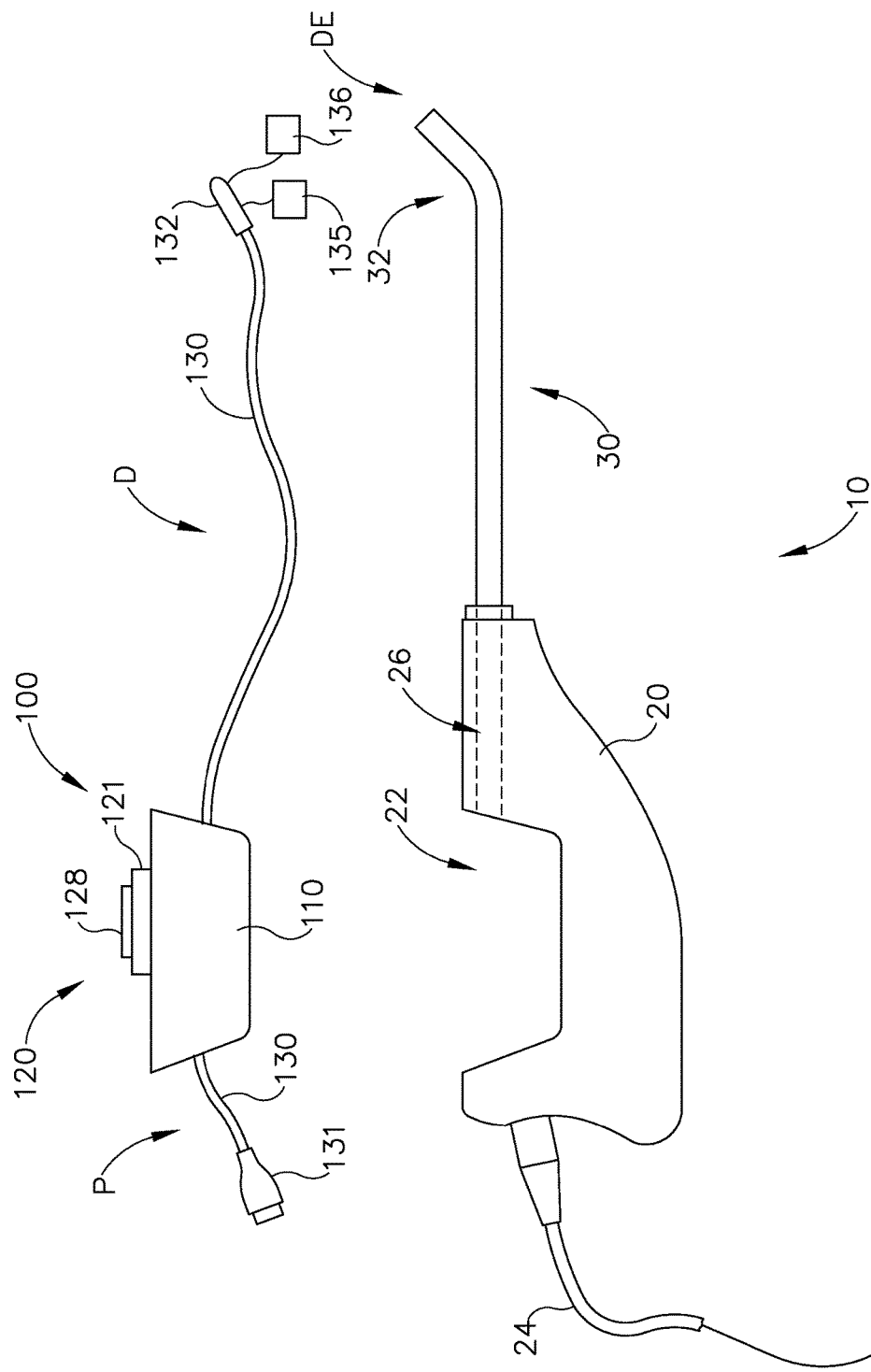
FIG. 6A depicts a side elevational view of the device of FIG. 1, with the cartridge of FIG. 2 spaced from a handle of the device.
Figure 6B:
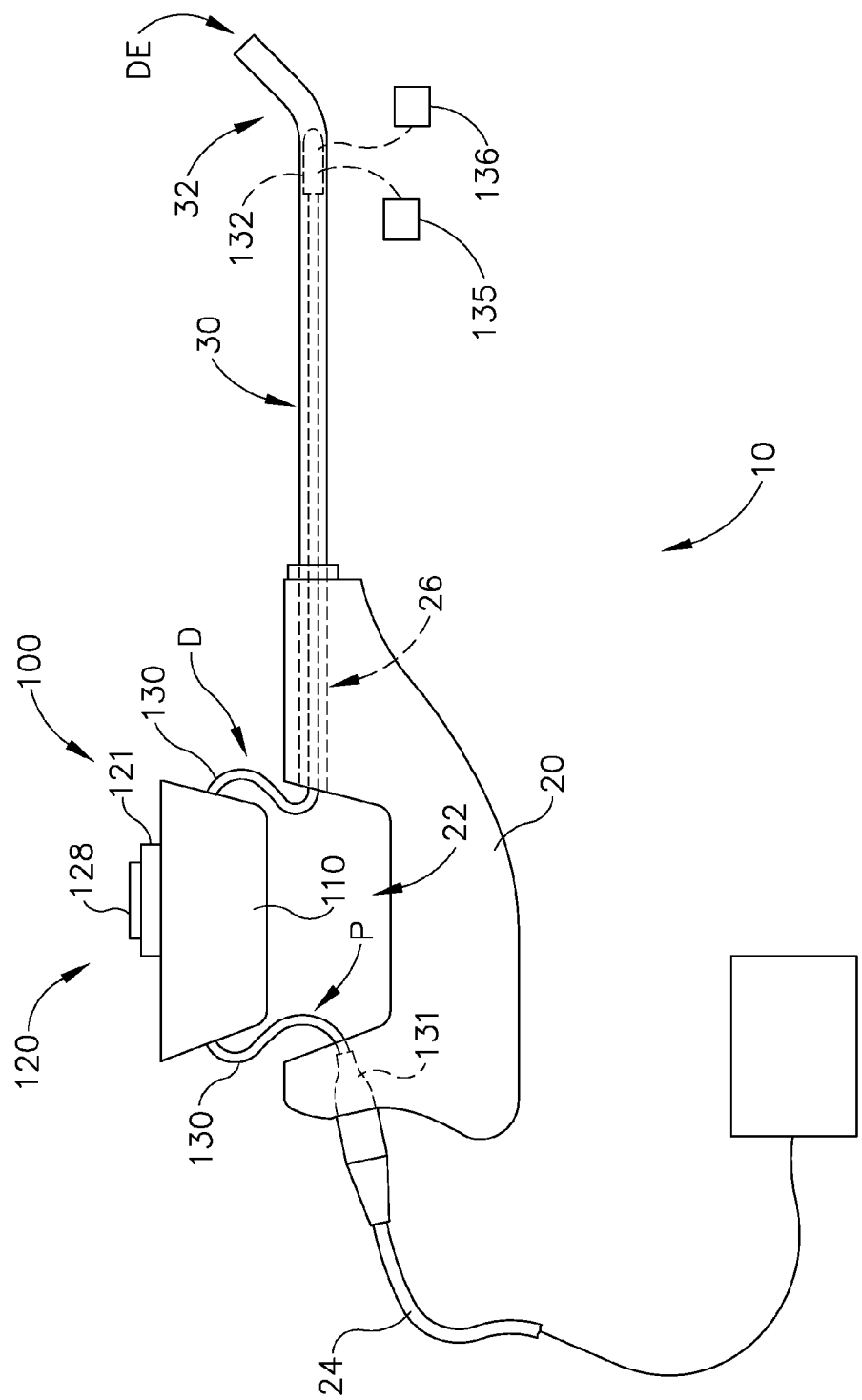
FIG. 6B depicts a side elevational view of the device of FIG. 1, with the cartridge of FIG. 2 moved toward the handle of the device, with a distal portion of the flexible wire of FIG. 3 positioned within a guide tube of the device, and with a proximal portion of the flexible wire coupled with a cable of the device.
Figure 6C:
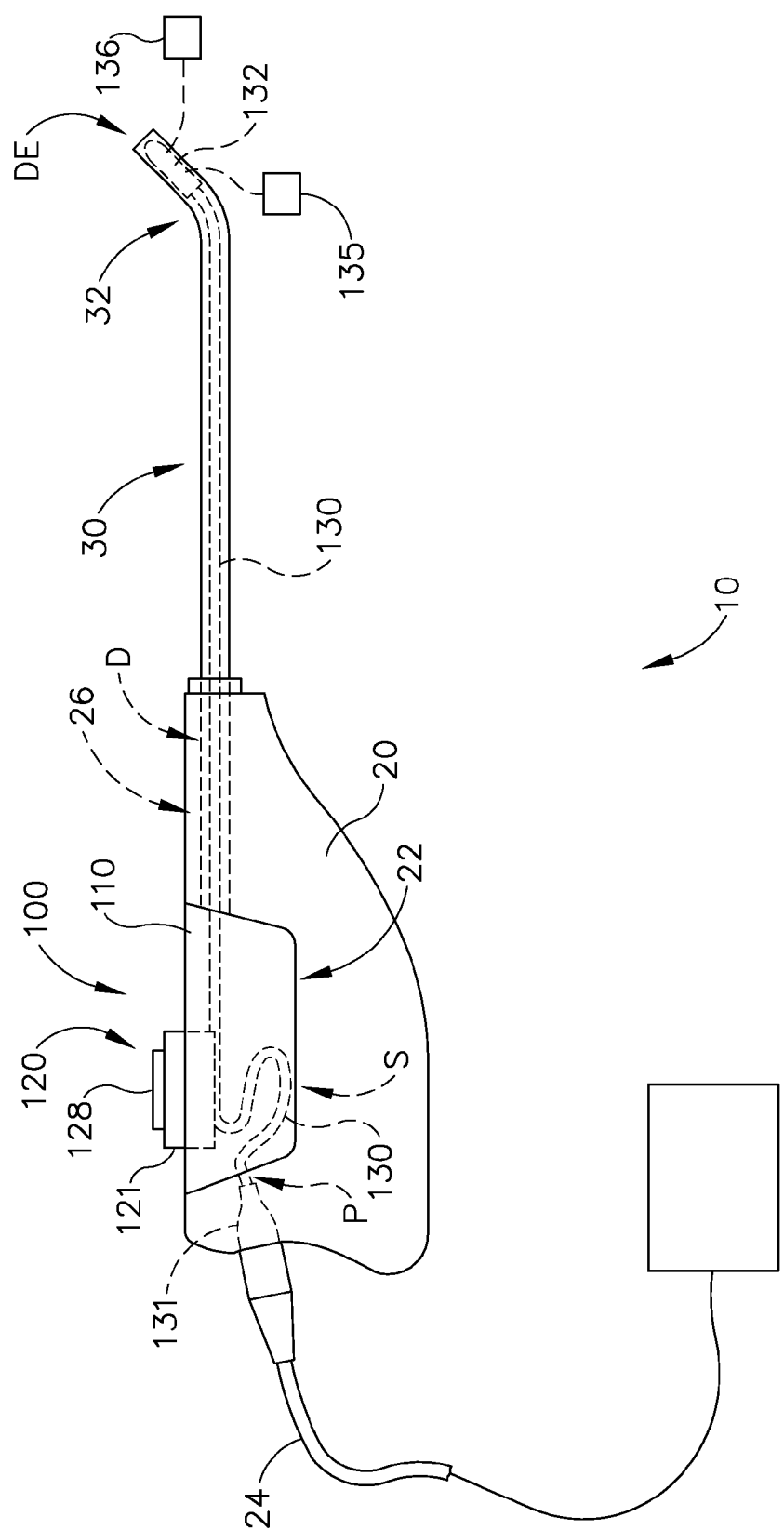
FIG. 6C depicts a side elevational view of the device of FIG. 1, with the cartridge of FIG. 2 coupled with the handle of the device, and with the flexible wire of FIG. 3 in a first longitudinal position.
Figure 6D:
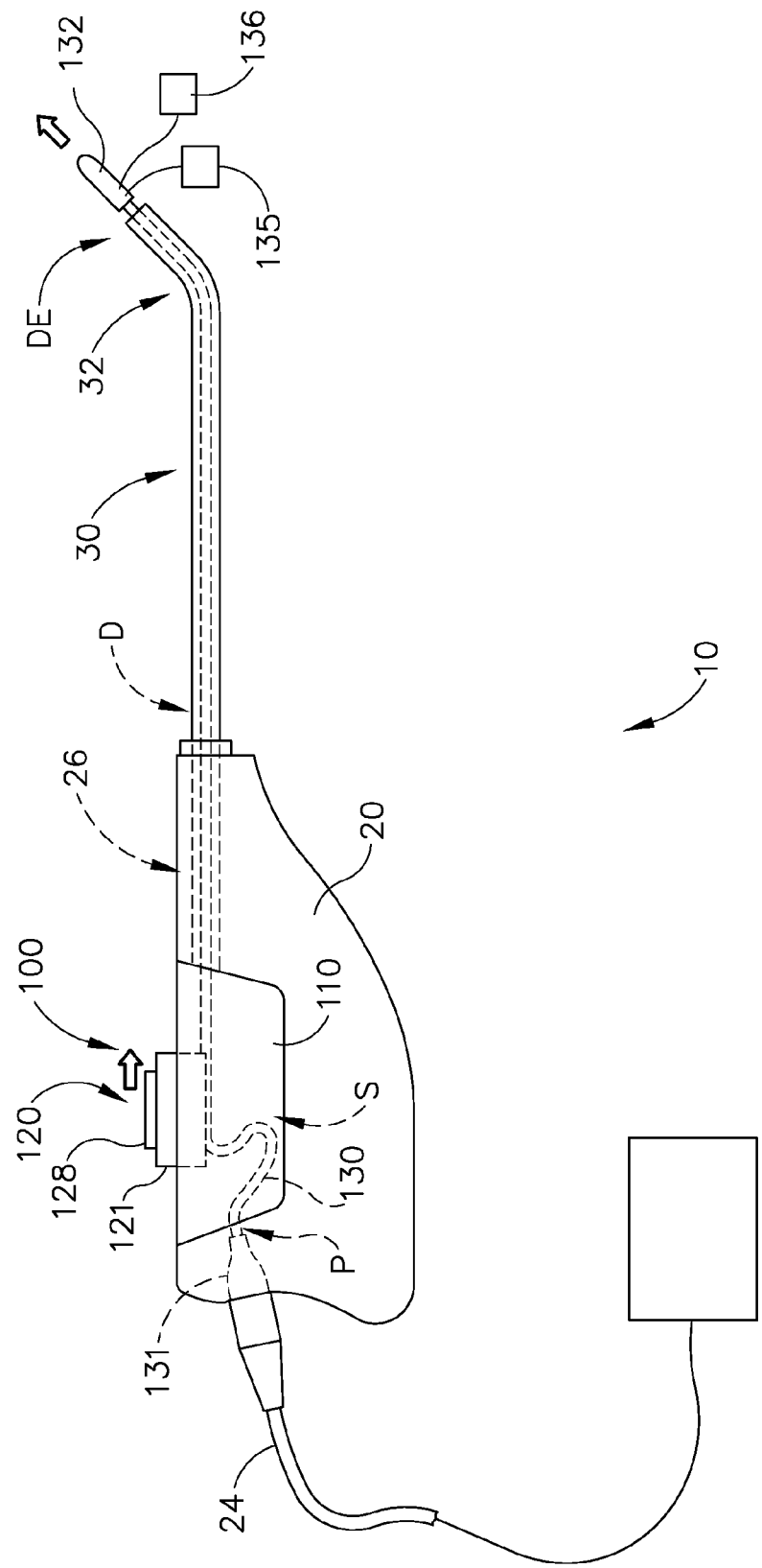
FIG. 6D depicts a side elevational view of the device of FIG. 1, with the cartridge of FIG. 2 coupled with the handle of the device, and with the flexible wire of FIG. 3 moved to a second longitudinal position.
Figure 6E:
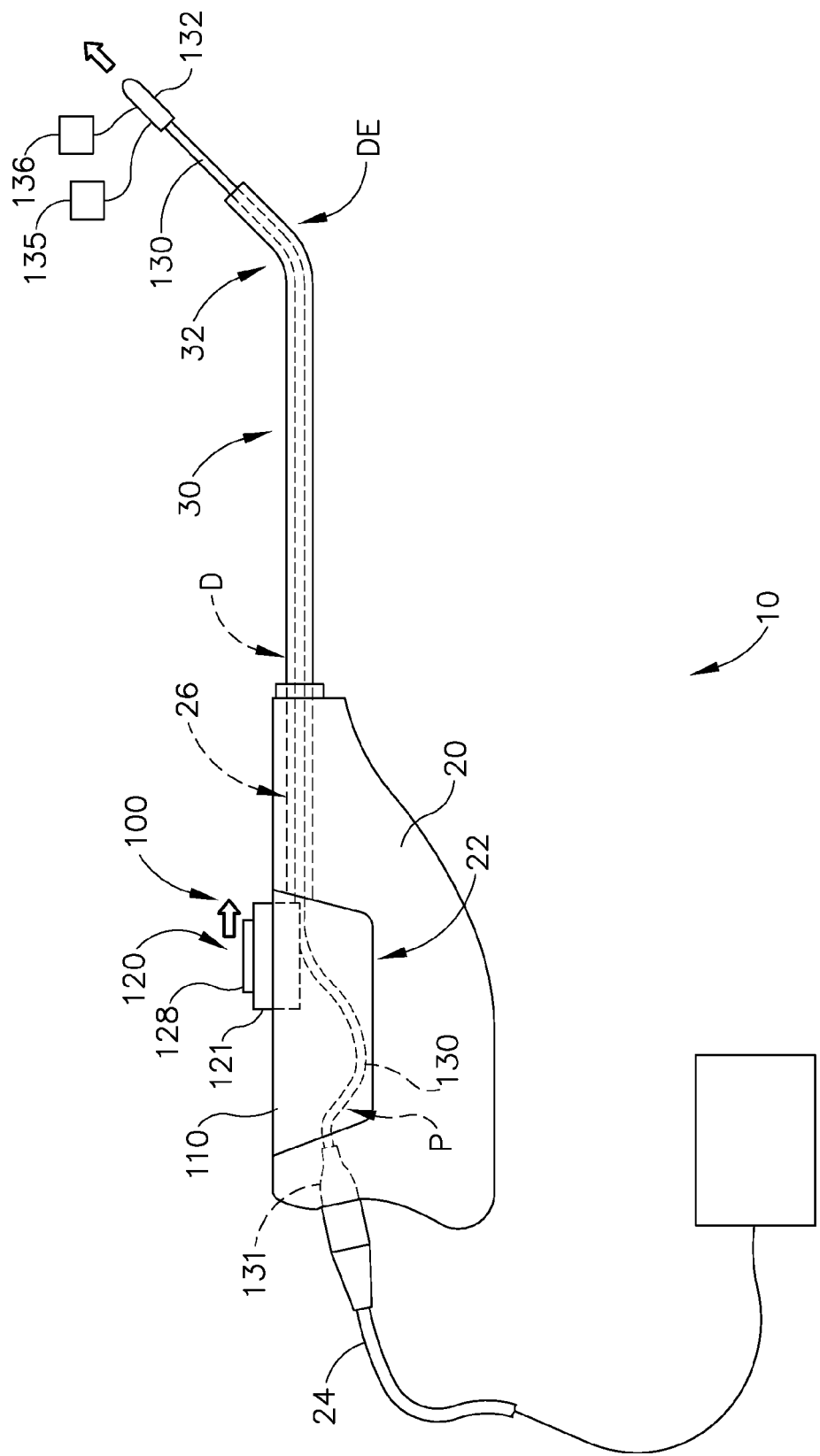
FIG. 6E depicts a side elevational view of the device of FIG. 1, with the cartridge of FIG. 2 coupled with the handle of the device, and with the flexible wire of FIG. 3 moved to a third longitudinal position.

FIGS. 6A-6E show an exemplary method of assembly and operation of device (10). FIG. 6A shows cartridge assembly (100) spaced apart from handle (20). As shown in FIG. 6B, as cartridge assembly (100) is moved toward handle (20), adapter (131) of proximal portion (P) of wire (130) is coupled with cable (24) of handle (20) and distal portion (D) of wire (130) is positioned within bore (26) of handle (20) and within the lumen of guide tube (30). FIG. 6C shows cartridge assembly (100) coupled within opening (22) of handle (20). Cartridge assembly (100) may couple within opening (22) of handle (20) in a snap-fit manner, interference-fit manner, friction-fit manner, or any other appropriate method. Cartridge assembly (100) and/or handle (20) may include latches, clasps, clamps, and/or any other suitable features to releasably secure cartridge assembly (100) relative to handle (20).

With actuator (120) in the proximal longitudinal position as shown in FIG. 6C, the tip of distal end (132) of wire (130) is positioned flush with the distal edge (34) of guide tube (30). As actuator (120) is translated distally to the intermediate longitudinal position as shown in FIG. 6D, distal end (132) of wire (130) extends from the distal end (DE) of guide tube (30), such that at least a portion of distal end (132) is distal to distal edge (34) of guide tube (30). In some versions, the length of wire (130) that extends distally past distal edge (34) of guide tube (30) at this stage is between 3 mm and 8 mm, or more particularly 5 mm. Alternatively, any other suitable length of wire (130) may extend distally past distal edge (34) of guide tube (30) at this stage. As actuator (120) is translated further distally to the distal longitudinal position as shown in FIG. 6E, distal end (132) of wire (130) extends further from the distal end (DE) of guide tube (30). In some versions, the length of wire (130) that extends distally past distal edge (34) of guide tube (30) at this stage is between 10 mm and 25 mm. Alternatively, any other suitable length of wire (130) may extend distally past distal edge (34) of guide tube (30) at this stage.

As will be described in more detail below, during use of device (10) in a patient, distal end (132) of wire (130) may contact one or more anatomical structures associated with the patient's paranasal sinuses and/or other anatomical structures (e.g., within the ear, nose, or throat, etc.). Wire (130) may have sufficient column strength to withstand buckling in response to longitudinally oriented forces when such contact occurs, at least when actuator (120) and wire (130) are in the intermediate longitudinal position shown in FIG. 6D. Wire (130) may additionally or alternatively be configured to buckle when such contact exceeds a threshold load. For instance, wire (130) may be configured to buckle when exposed to loads exceeding 7 Newtons of force, or any other appropriate force. It should also be understood that when actuator (120) and wire (130) are in the intermediate longitudinal position shown in FIG. 6D or in the distal longitudinal position shown in FIG. 6E, the length of wire (130) that is extended distally of distal edge (34) allows distal end (132) to deflect laterally when distal end (132) contacts one or more anatomical structures associated with the patient's paranasal sinuses and/or other anatomical structures. This may be useful when distal end (132) contacts a particularly fragile anatomical structure. In other words, the flexibility provided by wire (130) may prevent distal end (132) from inadvertently fracturing a fragile anatomical structure as distal end (132) is pushed against the fragile anatomical structure during a process of mapping or navigation as described herein.

It should be understood from the foregoing that device (10) may be provided in three different modes based on the longitudinal position of actuator (120) and wire (130). When actuator (120) and wire (130) are in the proximal position shown in FIG. 6C, device (10) is in a rigid mode. In the rigid mode, wire (130) does not provide any flexibility as distal end (132) contacts anatomical structures. When actuator (120) and wire (130) are in the intermediate position shown in FIG. 6D, device (10) is in a flexible mode. In the flexible mode, wire (130) provides an intermediate amount of "give" or flexibility as distal end (132) contacts anatomical structures. When actuator (120) and wire (130) are in the distal position shown in FIG. 6E, device (10) is in an extended mode. In the extended mode, wire (130) provides the most "give" or flexibility as distal end (132) contacts anatomical structures.

After device (10) is used in a patient, the operator may remove and discard cartridge assembly (100). The remaining components of device (10) may be sterilized for further use. After sterilization, another new cartridge assembly (100) may replace the discarded cartridge assembly (100) and device (10) may be used once again. Thus, in some versions of device (10), cartridge assembly (100) may be single-use.

II. EXEMPLARY MAPPING AND IMAGING SYSTEM AND METHOD

Figure 7:
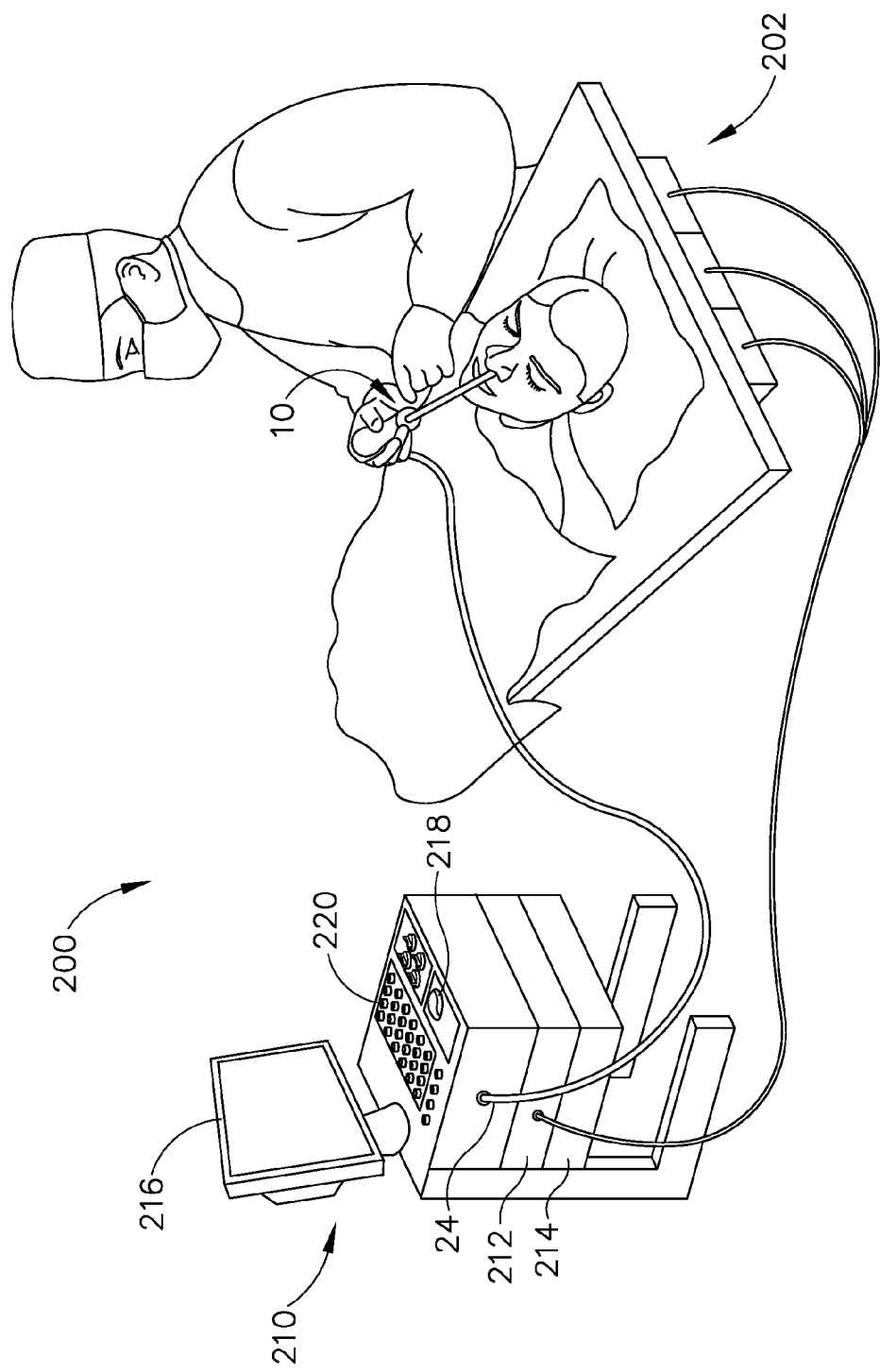
FIG. 7 depicts a schematic, pictorial illustration of a system for sinus mapping and imaging using the device of FIG. 1.
Figure 8A:
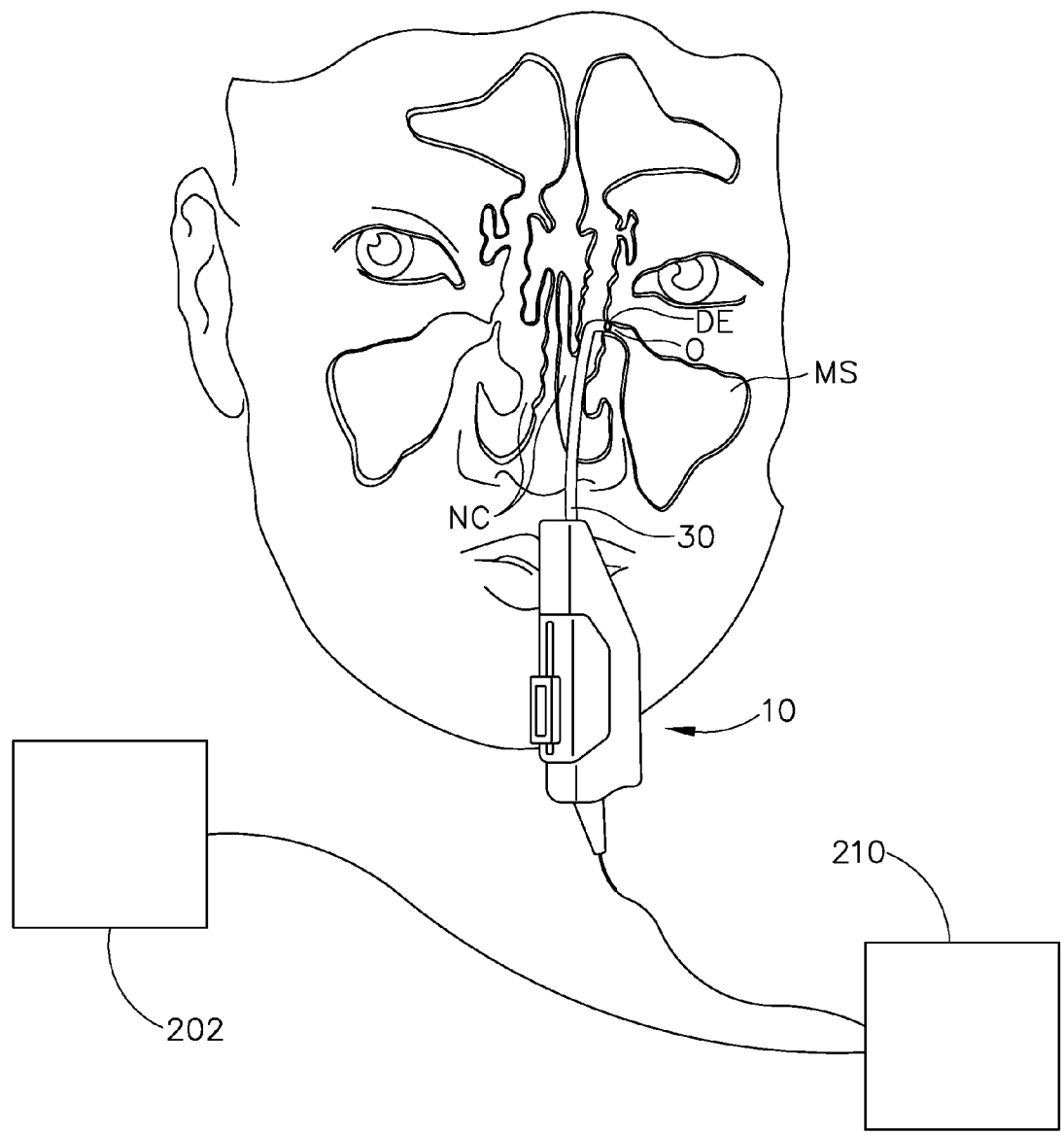
FIG. 8A depicts a front view of the device of FIG. 1 positioned adjacent an ostium of the maxillary sinus, with the flexible wire of FIG. 3 in the first longitudinal position of FIG. 6C.
Figure 8B:
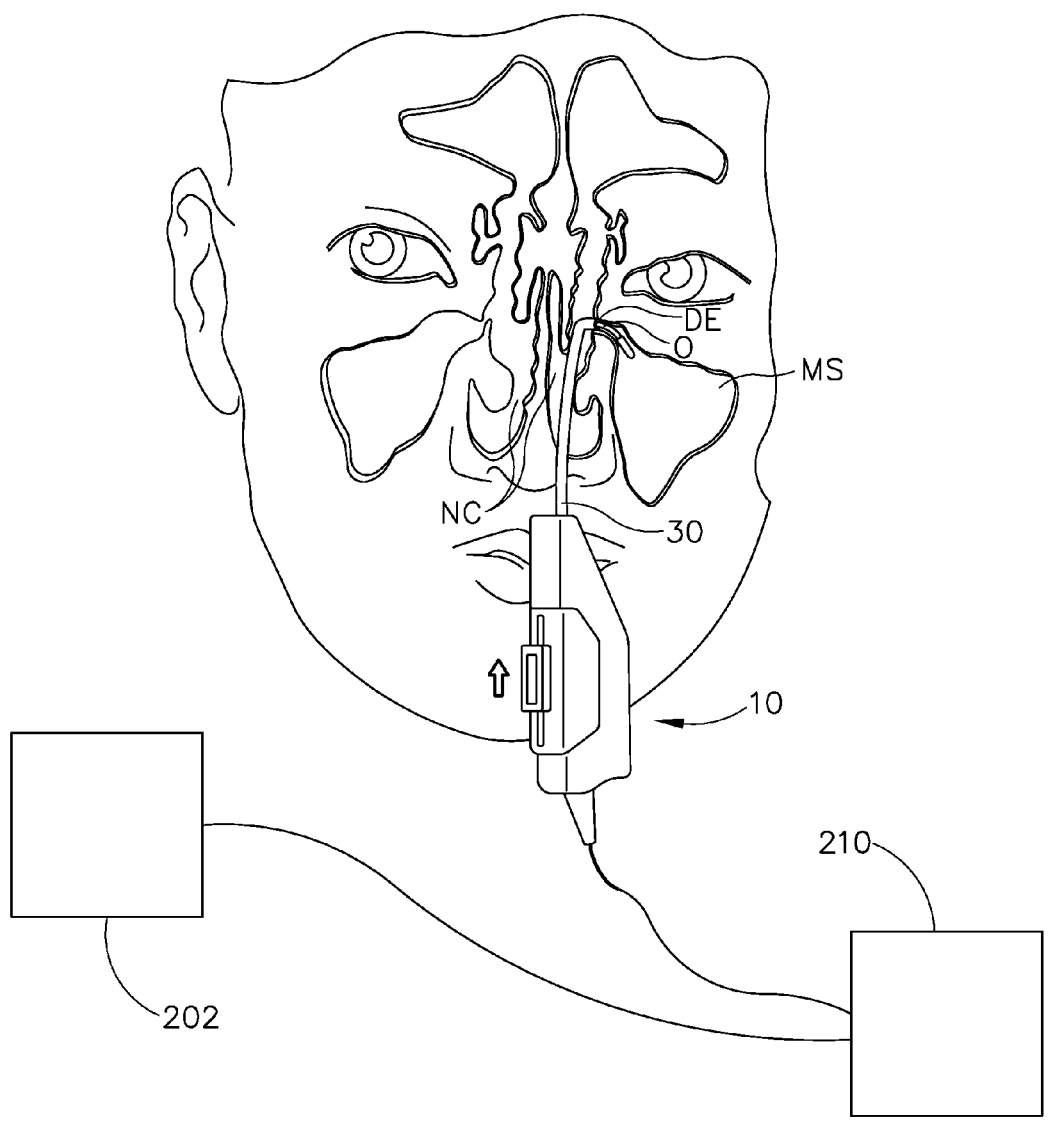
FIG. 8B depicts a front view of the device of FIG. 1 positioned adjacent an ostium of the maxillary sinus, with the flexible wire of FIG. 3 moved to the second longitudinal position of FIG. 6D.
Figure 8C:
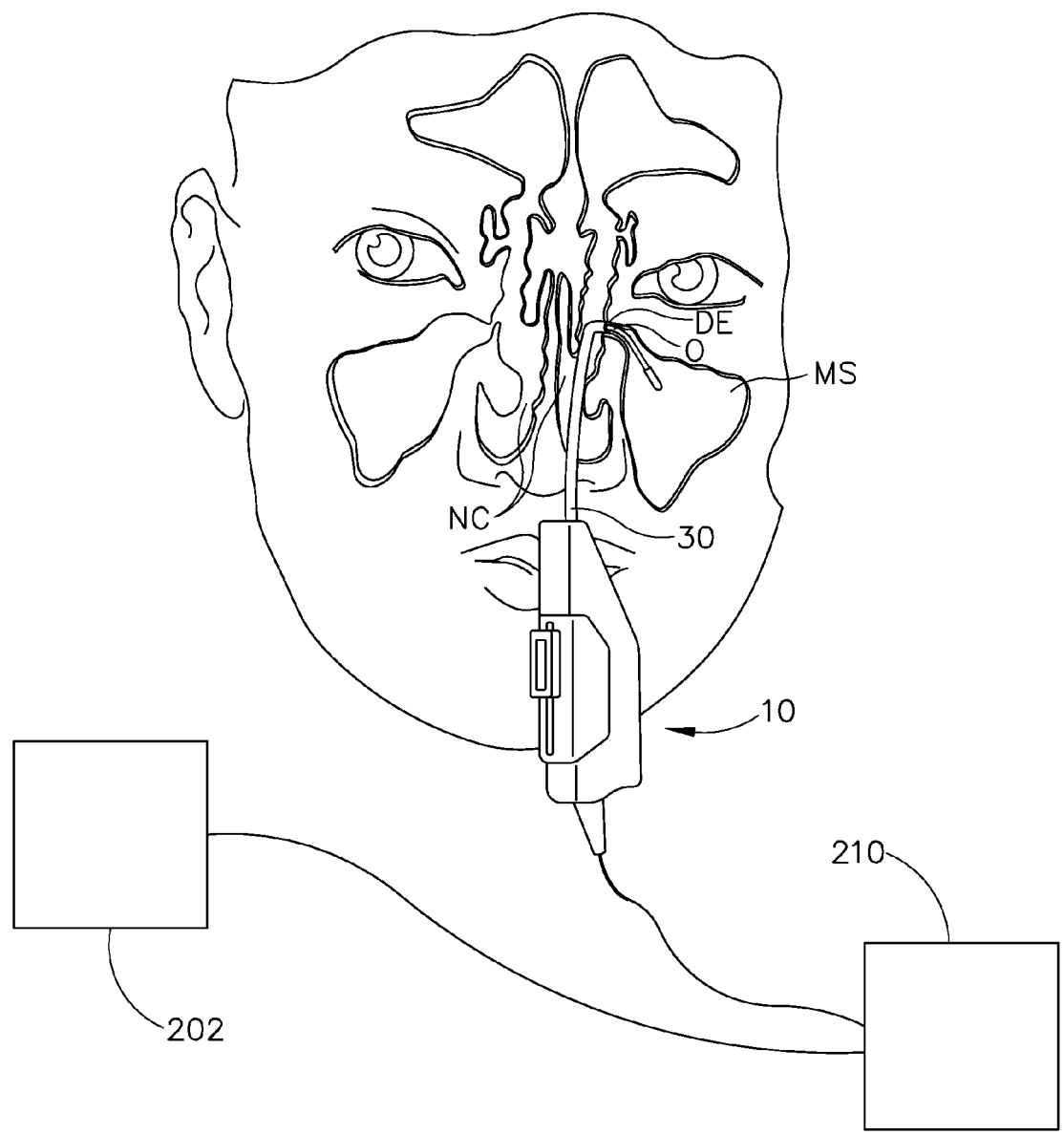
FIG. 8C depicts a front view of the device of FIG. 1 positioned adjacent an ostium of the maxillary sinus, with the flexible wire of FIG. 3 moved to the third longitudinal position of FIG. 6E.

An operator may wish to use device (10) to provide a 3-D image of a targeted anatomical structure. FIG. 7 is a schematic, pictorial illustration of an exemplary system (200) for imaging and mapping a target structure, such as the maxillary sinus (MS) of a patient. By way of example only, system (200) may be configured and operable in accordance with at least some of the teachings of U.S. Pat. No. 8,320,711, entitled "Anatomical Modeling from a 3-D Image and a Surface Mapping," issued Nov. 27, 2012, the disclosure of which is incorporated by reference herein. System (200) comprises device (10), which is inserted transnasally and advanced through the nasal cavity (NC) to position the distal end (DE) of guide tube (30) within or near the maxillary sinus (MS) as shown in FIG. 8A. After device (10) has been positioned, the operator advances wire (130) distally through guide tube (30) by translating actuator (120) distally such that distal end (132) of the wire (130) passes through the ostium (O) of the maxillary sinus (MS) and into the cavity of the maxillary sinus (MS) as shown in FIG. 8B (actuator (120) in the intermediate longitudinal position) and 8C (actuator (120) in the distal longitudinal position). It should be understood that the maxillary sinus (MS) is shown in the present example merely for illustrative purposes.

A positioning sub-system of system (200) comprises a set of external field generating coils (202). Field generating coils (202) are configured to generate electromagnetic fields in accordance with components and techniques known in the art. The locations of field generating coils (202) are defined in a fixed coordinate space of the positioning sub-system. In the present example, and as shown in FIG. 7, field generating coils (202) are located near the patient's head such that the patient's head is positioned in the electromagnetic field generated by field generating coils (202).

As mentioned above, distal end (132) of wire (130) of the present example comprises a position sensor (135). Based on the fields generated by coils (202), position sensor (135) generates position-related signals and transmits these signals to a console (210). A positioning processor (212) in console (210) calculates location coordinates of the distal end (132) of wire (130) from the position-related signals of position sensor (135). Distal end (132) of the wire (130) may be brought into contact with one or more locations on an inner surface of the maxillary sinus (MS), and the coordinates at each location are determined and stored in the console (210) as a matrix of points. The stored matrix is referred to hereinbelow as an anatomical map.

Distal end (132) of wire (130) may further comprise an ultrasound sensor (136) comprising a transducer that generates ultrasound energy and receives reflected ultrasound echoes. Based on the reflected echoes, ultrasound sensor (136) transmits ultrasound-related signals to an image processor (214) in console (210). Image processor (214) may receive these ultrasound-related signals from multiple positions and orientations of the ultrasound sensor (136), and processes these signals to construct a 3-D ultrasound image in a 3-D space, comprising a set of voxels (i.e., 3-D pixels). Image processor (214) may be configured to perform other functions such as contour delineation. Using 3-D visualization techniques, image processor (214) also displays 3-D objects (such as delineated contours) on a display (216) of console (210).

Console (210) may be interactive, enabling the operator to control displayed items using a pointing device, such as a track-ball or mouse (218), and/or to enter commands with a keyboard (220). In some instances, the operator may use mouse (218) and/or keyboard (220) to mark and/or annotate certain anatomical features or regions within the image displayed through display (216).

In the present example, the functions of the positioning processor (212) and image processor (214) are implemented using a general-purpose computer that is programmed in software to carry out the functions described herein. The software may be downloaded to the computer in electronic form, over a network, for example, or it may alternatively be supplied to the computer on tangible media, such as CD or DVD, etc. The positioning processor (212) and image processor (214) may be implemented using separate computers or using a single computer, or may be integrated with other computing functions of system (200). Additionally or alternatively, at least some of the positioning and image processing functions may be performed using dedicated hardware.

Figure 9:
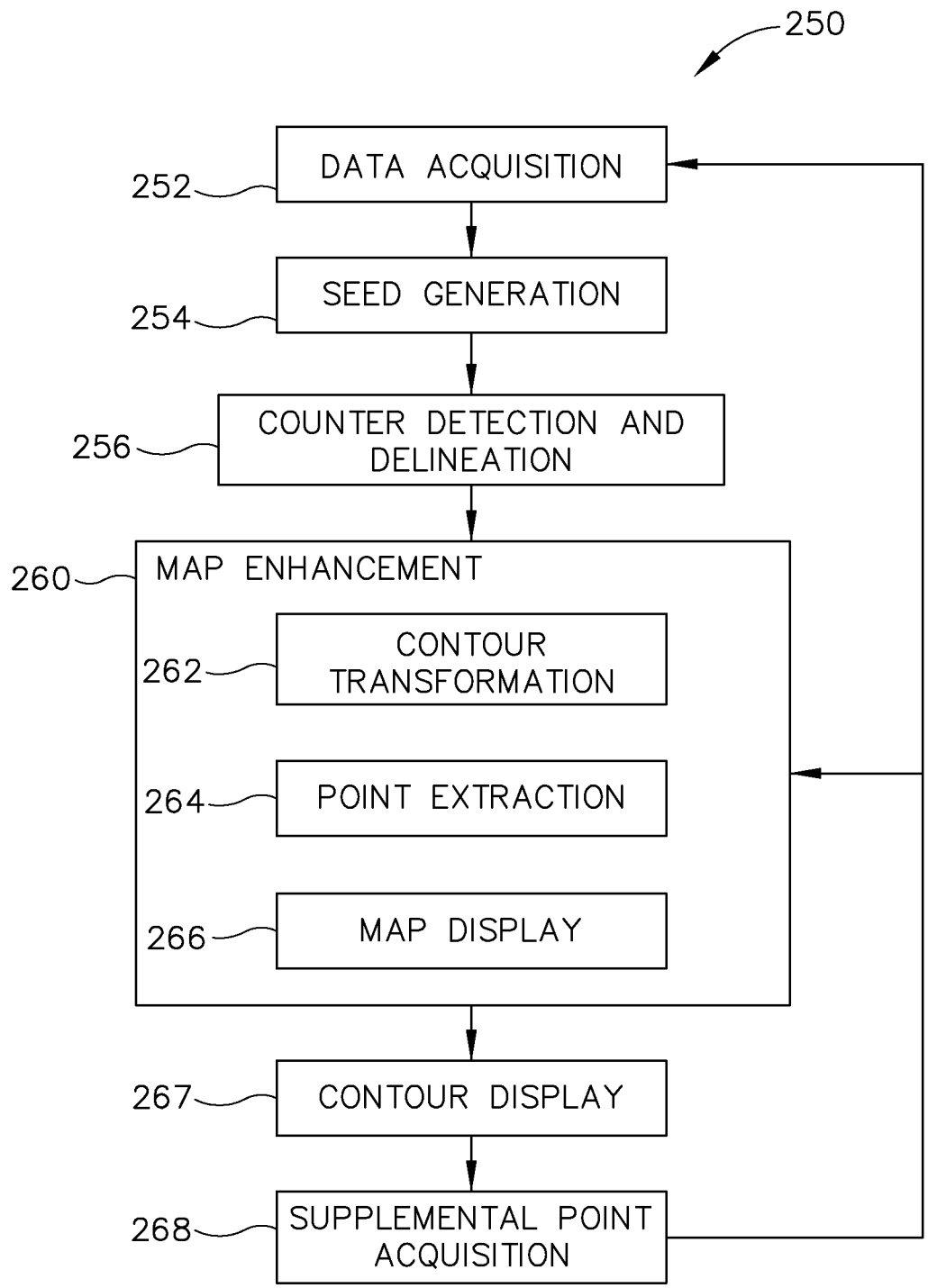
FIG. 9 depicts a flow chart that schematically illustrates a method for sinus mapping and imaging.

FIG. 9 is a flow chart that schematically illustrates an exemplary process (250) for mapping and imaging of a target structure, such as the maxillary sinus (MS) of a patient. At a data acquisition step (252), a user manipulates device (10) within the maxillary sinus (MS) to acquire ultrasound image data and anatomical map data of a target structure via position sensor (135) and ultrasonic sensor (136). The anatomical map data may be delineated by a user of system (200). Additionally or alternatively, the anatomical map data may be acquired by contact mapping, such as electro-anatomical mapping, in which distal end (132) of wire (130) is brought into contact with multiple points on the inner surface of the maxillary sinus (MS).

At a seed generation step (254), image processor (214) automatically generates, from the anatomical map data, one or more seed points. A seed point may be a particular point comprised in the map, or may be determined by interpolation and/or extrapolation from several measured points. In some instances, a surface may be generated by a polynomial least-squares fit of points in the anatomical map, and a single seed point is determined as a midpoint of the surface. Alternatively, the seed point may be chosen by an operator of system (200).

Next, at a contour detection step (256), a contour in the ultrasound image is detected and delineated based on the seed point(s). The contour may correspond to the inner surface of the maxillary sinus (MS). Contour detection and delineation is based on the seed point(s). Detection may include edge detection methods, correlation methods, motion detection methods and other methods known in the art. A well-known method of edge detection is the "Canny" edge detection method, described in F. J. Canny, "A Computational Approach to Edge Detection," *IEEE Trans PAMI*, 8(6):679-698, 1986. An improved method, based on the "Canny" edge detection method, is described in U.S. Pub. No. 2009/0080738, entitled "Edge Detection In Ultrasound Images," published Mar. 26, 2009, now abandoned, the disclosure of which is incorporate by reference herein. The output of step (256) is a matrix in three dimensions defining one or more contours that segment the original ultrasound 3-D image produced by image processor (214). Alternatively, contours may be defined using parametric equations. Once a contour is determined according to the above steps, the contour may be applied in subsequent steps of visualizing the ultrasound image and the anatomical map.

At a map enhancement step (260), the resolution of the anatomical map acquired at step (252) is enhanced with points extracted from the contour. Step (260) comprises three sub-steps. At a sub-step (262), the contour determined at step (256) is transformed in the 3-D coordinate space to align with the points in the electro-anatomical map. In one embodiment, the transformation of the contour is performed based on a least-squares, best-fit algorithm.

Subsequently, at a point extraction sub-step (264), contour points are extracted from the transformed contour and added to the anatomical map, thereby enhancing the density of the map. Extraction of contour points may be performed automatically by projecting a 2-D grid of a given density onto the surface of the contour and extracting points at grid intersections.

At a sub-step (266), a picture of the enhanced map, including coordinates of the extracted contour points, is displayed. The picture is generally displayed as a 3-D image using 3-D visualization methods, including projection of 3-D data onto the 2-D plane of display (216). Typically, the displayed image may be rotated via track-ball or mouse (218) and/or keyboard (220) so as to be viewed from multiple perspectives.

At a contour display step (267), the contour determined at step (256) is displayed, using 3-D visualization methods. Physiological parameters from the anatomical map may be interpolated and/or extrapolated over the surface of the contour so as to display the contour with highlighting indicative of the parametric values. Highlighting may be indicated by various means, such as coloring or shading. Similar highlighting of the contour surface may also be used to display image data (i.e., voxels) from the 3-D ultrasound image. Each point of the contour surface may be highlighted according to the value of the voxel at the corresponding coordinates in the 3-D image. The contour may also be highlighted based on 3-D image data extracted from other sources, including MRI, CT, or x-ray imaging. The contour may also be transformed by a given radial offset, and the 3-D image data highlighting may be displayed according to the offset coordinates, analogous to viewing onion skins at various depths.

In further examples, image processor (214) may generate a closed volume, rather than a surface, based on the contour. Within the closed volume, voxels extracted from 3-D image sources may be displayed with various degrees of transparency, such that voxels corresponding to unobstructed anatomical structures appear transparent and voxels corresponding to tissues or other obstructions appear relatively dark and opaque.

At a supplemental acquisition step (268), additional map points are measured with wire (130) and added to the anatomical map, thereby increasing the map density.

Process (250) may be performed iteratively, in real-time, such that images displayed via display (216) of console (210) are updated based on newly acquired data and subsequent calculations based on the newly acquired data.

III. EXEMPLARY NAVIGATING METHOD

As noted above, mapping and navigational device (10) may be used in conjunction with system (200) to provide image-guided navigation within a patient. Distal end (132) of wire (130) may be used to gently probe anatomical structures within the patient, which will allow for identification of anatomic structures that can be directly visualized in the endoscopic view and anatomical structures that are outside of the endoscopic view using position sensor (135). Device (10) could be used to identify any portion of the anatomy, including structures and spaces within the nasal anatomy such as the frontal outflow tract and cells within the frontal recess, ethmoid cells, sinus ostia, the skull base, optic nerve, carotid artery, etc. via gentle probing to prevent damage to mucosa and anatomic structures. Distal end (132) of wire (130) may identify anatomical structures and the navigation software of system (200) could use this location information to generate a computer-rendered endoscopic view via display (216), as observed from distal end (132) of wire (130). This would allow visualization of a rendered endoscopic view from the distal end (132) of wire (130) to observe sinus outflow tracts, ostia, and walls of the sinus cavities, etc. In some versions as will be described in greater detail below, a modified version of device (10) also provides suction to remove blood, mucus, and other fluids from the surgical field. With wire (130) in the retracted position, device (10) acts as a standard navigable probe and/or, in the variation of device (10) described below, a suction device.

After the 3-D map or image has been generated as described above, the operator may wish to use device (10) as a navigation tool. As mentioned above, distal end (132) of wire (130) of the present example comprises a position sensor (135). Based on the fields generated by coils (202), position sensor (135) generates position-related signals and transmits these signals to a console (210). Positioning processor (212) calculates location coordinates of the distal end (132) of wire (130) from the position-related signals of position sensor (135). Console (210) correlates the data it receives from position sensor (135) and positioning processor (212) with the 3-D image. The 3-D image is displayed on display (216) along with an indicator (e.g., cross hairs or an illuminated dot) showing the real time position distal end (132) of wire (130) relative to the anatomical structures shown in the 3-D image. In this manner, the operator is able to know the precise position of distal end (132) by viewing display (216) of console (210), even if the operator is unable to directly visualize distal end (132) at its current location within the body.

In view of the foregoing, it should be understood that wire (130) may be incorporated into various kinds of instruments in order to provide navigation of such instruments in relation to 3-D images or maps that are generated as described herein. Such alternative instruments may also be used to generate 3-D images or maps that are generated as described herein. In other words, it is contemplated that the wire (130) and its associated functionality may be readily incorporated into various instruments other than device (10). By way of example only, wire (130) and its associated functionality may be readily incorporated into otherwise conventional suction devices, otherwise conventional probe devices, otherwise conventional seeker devices, etc. Incorporating wire (130) and its associated functionality into an otherwise conventional instrument may enhance such an instrument by facilitating use of the instrument around fragile anatomical structures such as those found within the nasal cavity, etc. In other words, the flexibility provided by wire (130) may prevent distal end (132) from inadvertently fracturing a fragile anatomical structure as distal end (132) is pushed against the fragile anatomical structure when the instrument incorporating wire (130) is used during a process of mapping or navigation as described herein. In the absence of the flexibility provided by wire (130), the conventional instrument might otherwise fracture the fragile anatomical structure. This enhanced usability provided by wire (130) around fragile anatomical structures may be particularly beneficial when distal end (132) is located in a region that is outside of an endoscopic field of view, where the operator would otherwise be operating the instrument blindly.

IV. EXEMPLARY MAPPING AND NAVIGATIONAL DEVICE WITH MALLEABLE GUIDANCE TUBE AND SUCTION FEATURES

Figure 10:
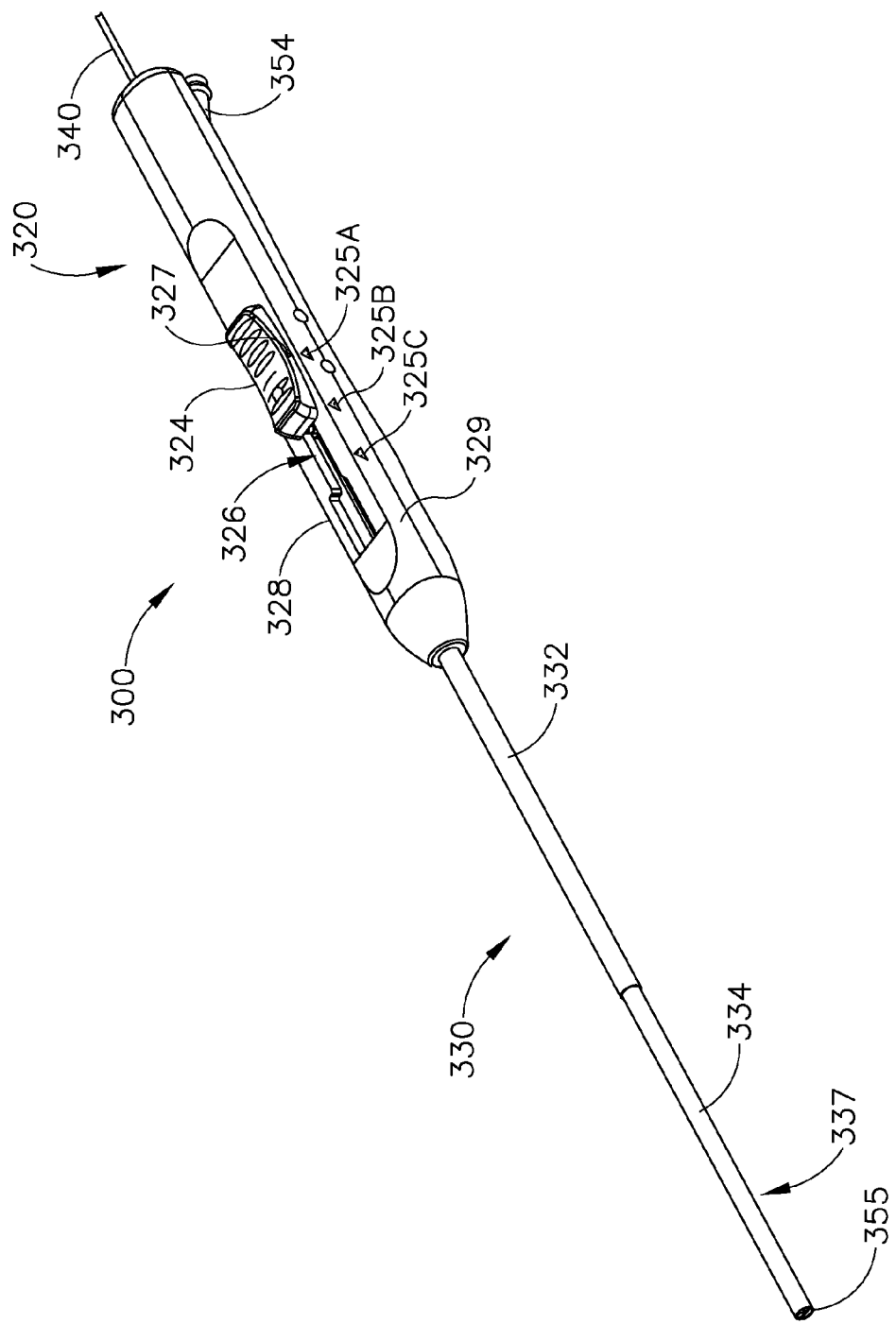
FIG. 10 depicts a perspective view of another exemplary mapping and navigation device.
Figure 11:
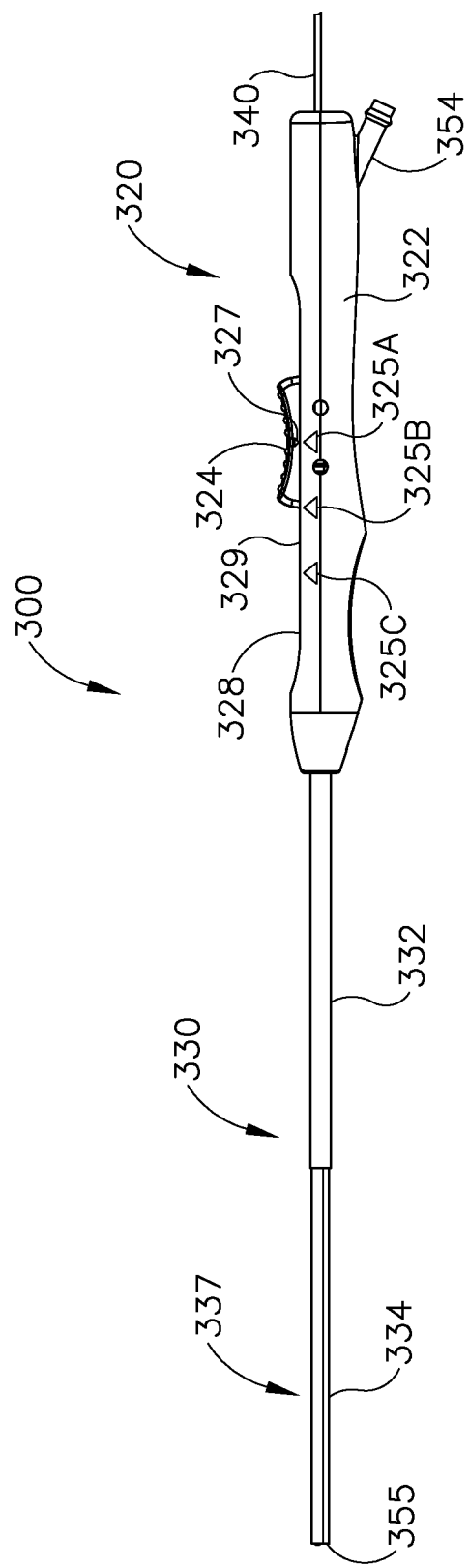
FIG. 11 depicts a side elevational view of the device of FIG. 10.

FIGS. 10 and 11 show another exemplary mapping and navigational device (300) that may be used in conjunction with system (200) and in addition to or in lieu of device (10) described above, to map and/or navigate the nasal cavity of a patient, passageways associated with the nasal cavity of a patient (e.g., paranasal sinus ostia and cavities, the frontal recess, the Eustachian tube, etc.), and/or other anatomical passageways (e.g., within the ear, nose, or throat, etc.). Mapping and navigational device (300) of the present example comprises a handle assembly (320) and a guide tube assembly (330). In the present example, the combination of handle assembly (320) and a guide tube assembly (330) is provided as a disposable device (e.g., single patient only, non-sterilizable). In some instances, the combination of handle assembly (320) and a guide tube assembly (330) is provided as a reusable device (e.g., multi-patient, sterilizable). Handle assembly (320) of the present example may be grasped like a pencil by a user. Alternatively, various other suitable configurations and gripping techniques may be used, including but not limited to a pistol grip configuration or a power grip technique.

Figure 14:
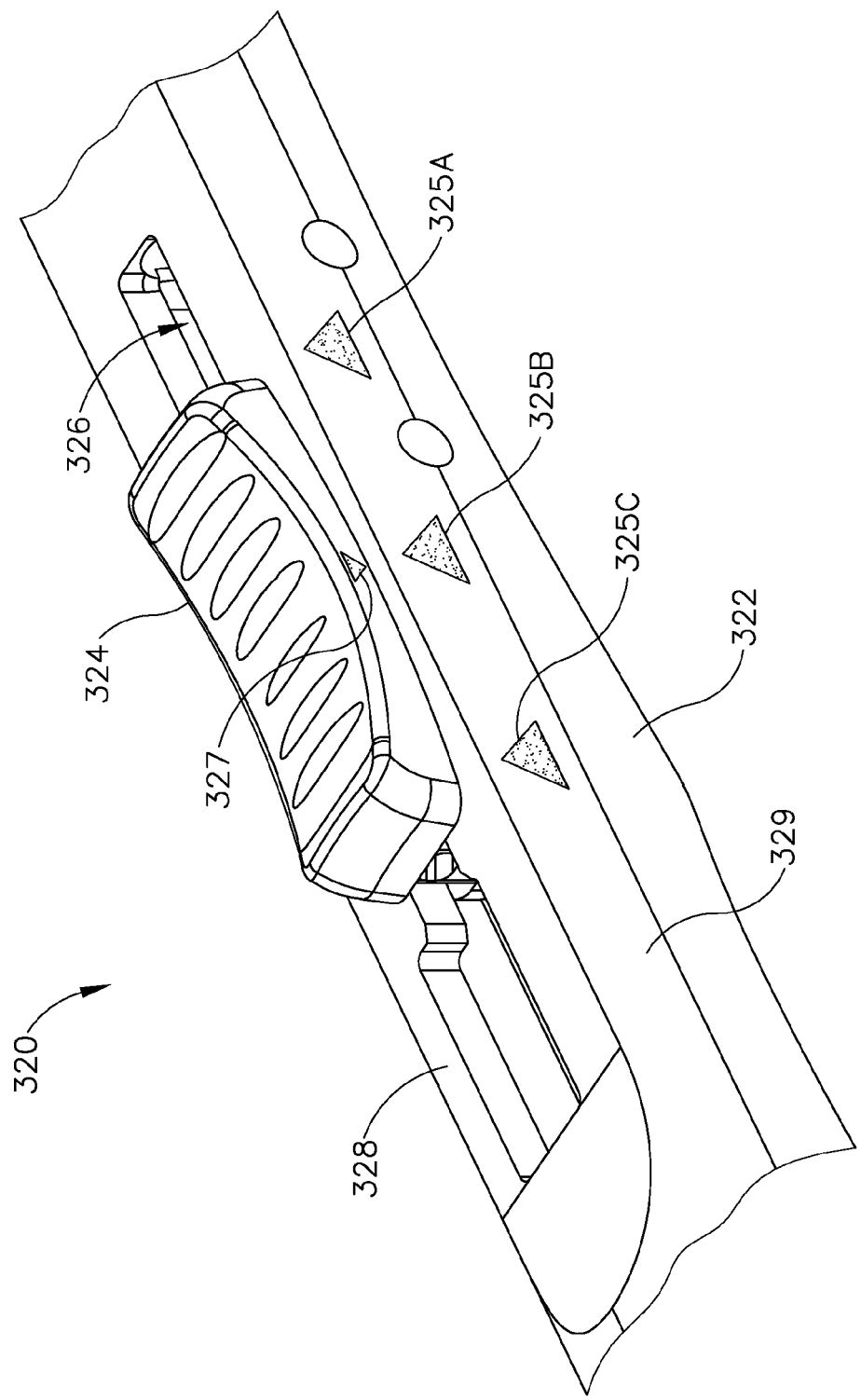
FIG. 14 depicts a detailed perspective view of a handle assembly of the device of FIG. 10.

Handle assembly (320) comprises a body (322), a manual actuator (324), and a flexible wire (340). As best seen in FIG. 14, body (322) includes a longitudinal slot (326) formed in a top surface (328) of body (322). Actuator (324) is slidably disposed within slot (326) of body (322) via a pair of longitudinal channels (not shown) formed in opposing sides of actuator (324) such that, as will be described in more detail below, actuator (324) is configured to translate within slot (326) between a proximal longitudinal position (FIG. 18A), an intermediate longitudinal position (FIG. 18B), and a distal longitudinal position (FIG. 18C). Top surface (328) of body (322) includes a series of visible markers (325A, 325B, 325C) positioned along a side surface (329) of body (322) adjacent slot (326). Markers (325A, 325B, 325C) correspond to the proximal longitudinal position, the intermediate longitudinal position, and the distal longitudinal position of actuator (324), respectively. Actuator (324) includes a visible marker (327) that is configured to align with markers (325A, 325B, 325C) of body (322) to visually indicate that actuator (324) has reached each corresponding longitudinal position. Additionally, or alternatively, body (322) and/or actuator (324) may further include features (e.g. mechanical detents) that are configured to provide tactile and/or audible feedback to the operator as actuator (324) reaches each longitudinal position. Of course, body (322) and/or actuator (324) may simply lack markers (325A, 325B, 325C, 327) and/or mechanical detents altogether, as such components are merely optional and not required. It should also be appreciated that although not depicted, actuator (324) may include a rotatable member configured to operate substantially similar to rotatable member (128) of actuator (120) described above.

Figure 12:
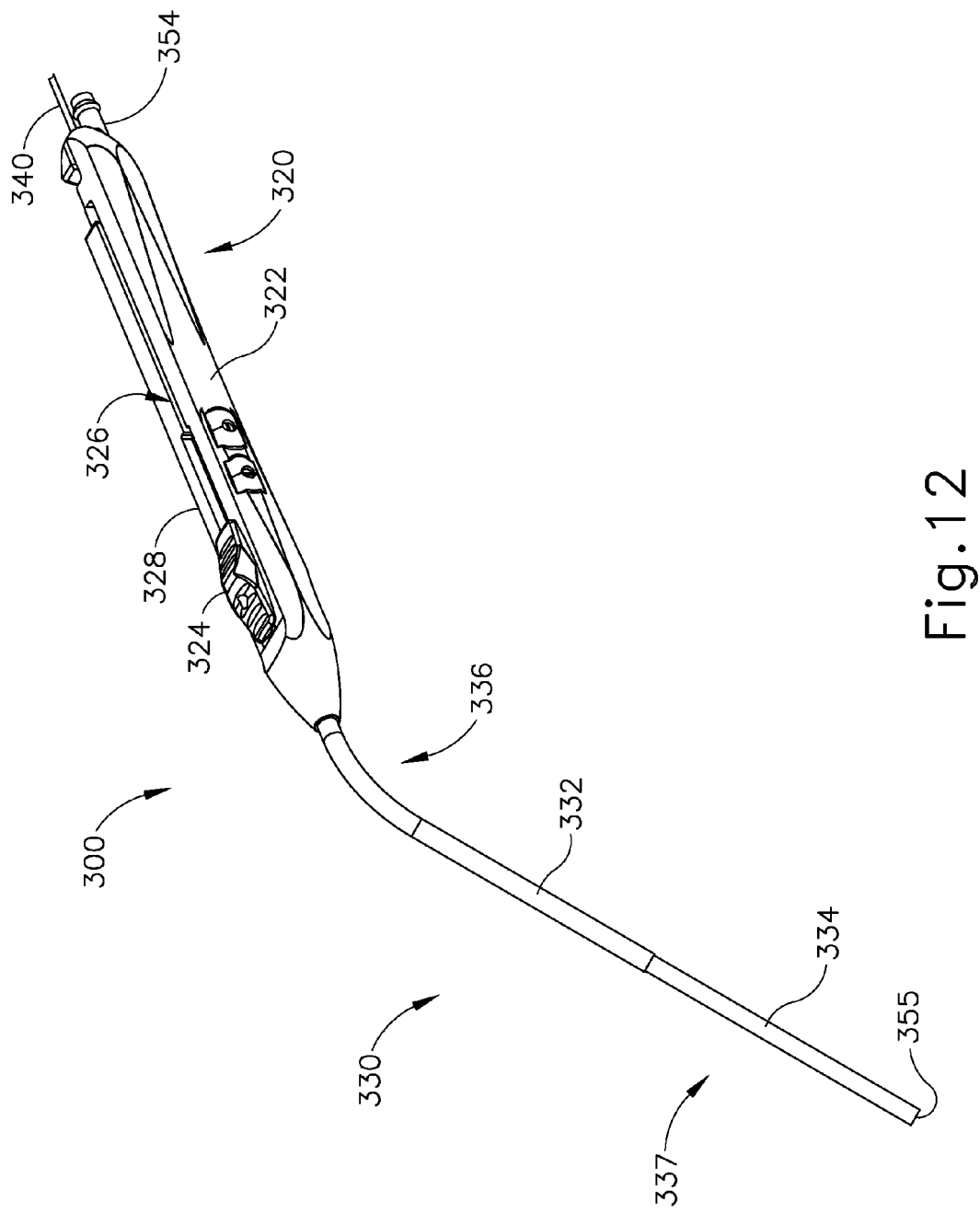
FIG. 12 depicts a perspective view of yet another exemplary mapping and navigation device.
Figure 13:
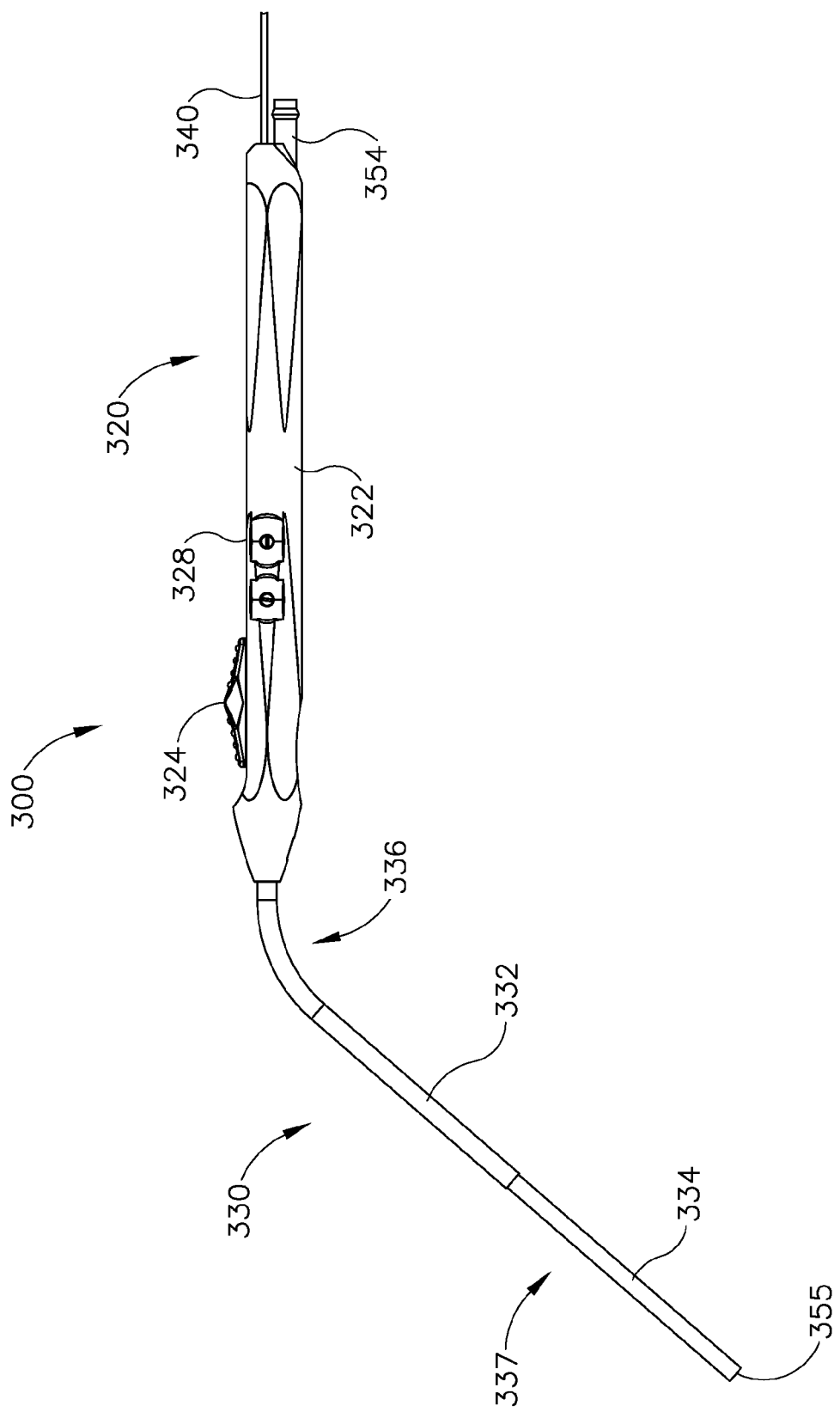
FIG. 13 depicts a side elevational view of the device of FIG. 12.

Guide tube assembly (330) extends distally from handle assembly (320). Guide tube assembly (330) of the present example includes an outer sheath (332) and an inner tube (334) Inner tube (334) is positioned within and extends distally from outer sheath (332) such that a proximal length (351) of inner tube (334) is encased within outer sheath (332) (FIG. 16) and such that a distal length (337) of inner tube (334) is exposed relative to outer sheath (332). In the present example, outer sheath (332) is rigid such that proximal length (351) of inner tube (334) positioned within outer sheath (332) conforms to the shape of outer sheath (332). In some versions of device (300), outer sheath (332) is substantially straight as shown in FIGS. 10 and 11. Alternatively, outer sheath (332) may include a preformed bent portion (336) as shown in FIGS. 12 and 13. By way of example only, bent portion (336) may provide a bend angle of approximately 20°. Alternatively, any other suitable bend angle may be used.

In the present example, inner tube (334) is malleable such that the operator may deform distal length (337) of inner tube (334) to any desired bend angle and distal length (337) may maintain the selected bend angle during subsequent use. By way of example only, distal length (337) may have a length of between approximately 0.5 inches and approximately 3.0 inches. Alternatively, any other suitable length may be used. In some versions, inner tube (334) extends along the full length of device (300). Regardless of the length of inner tube (334), inner tube (334) may be reinforced with a metal or plastic braid or coil positioned about or within inner tube (334). In some versions of guide tube assembly (330), outer sheath (332) may be omitted entirely such that the entire length of guide tube assembly (330) is malleable. In other versions of guide tube assembly (330), outer sheath (332) may extend the entire length of inner tube (334) or inner tube (334) may be omitted entirely such that the entire length of guide tube assembly (330) is rigid. In still other versions of guide tube assembly (330), guide tube assembly (330) is configured similar to the Relieva Flex™ Sinus Guide Catheter by Acclarent, Inc. of Menlo Park, Calif. As yet another merely illustrative example, guide tube assembly (330) may consist of a single tubular element instead of two tubular elements such as inner tube (334) and outer sheath (332). For instance, guide tube assembly (330) may comprise a single tubular element with materials of disparate stiffness, such that a proximal region of the single tubular element is rigid while a distal region of the single tubular element is malleable. As yet another merely illustrative example of a single tubular element version, the single tubular element may be formed of a stiff material such as metal with a distal portion being annealed to make the distal portion of the single tubular element malleable. Other suitable forms that guide tube assembly (330) may take will be apparent to those of ordinary skill in the art in view of the teachings herein.

Figure 15:
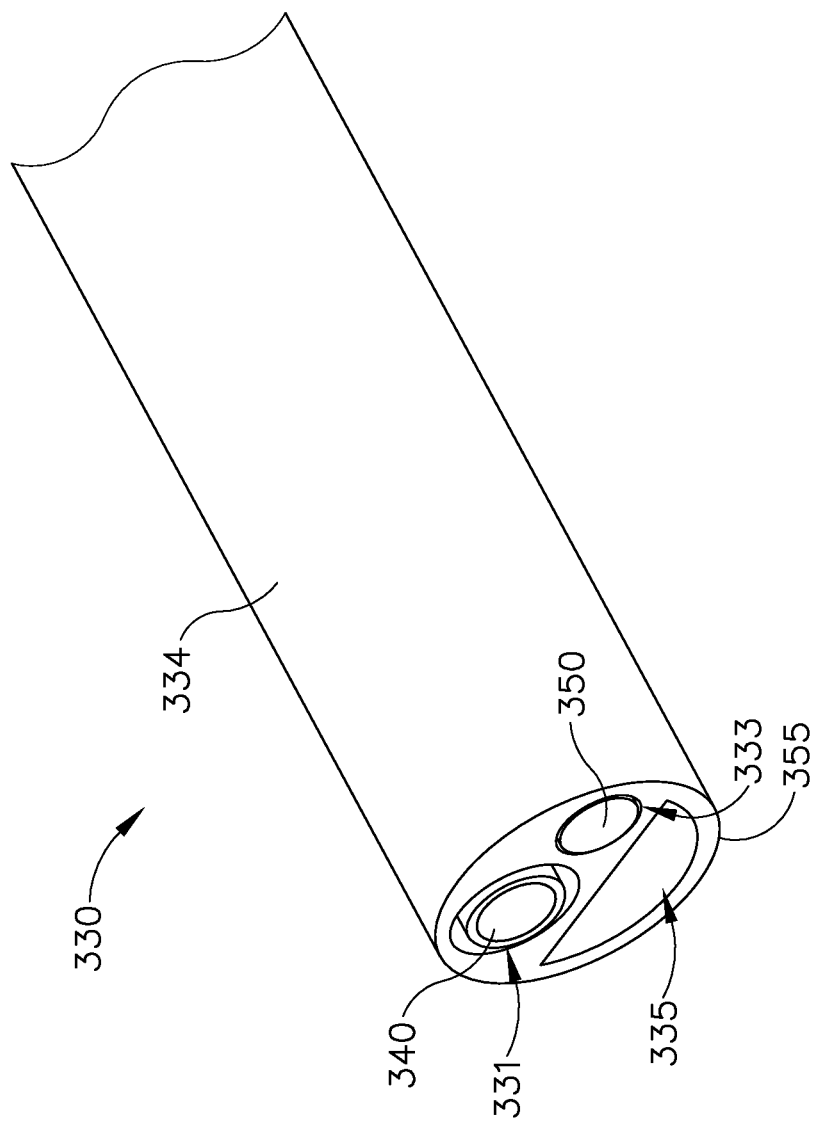
FIG. 15 depicts a detailed perspective view of a distal end of a guide tube of the device of FIG. 10.

As best seen in FIG. 15, inner tube (334) includes a plurality of lumens (331, 333, 335) formed therein and which extend the full length of inner tube (334). As will be described in more detail below, lumen (331) is configured to slidably receive wire (340) such that lumen (331) is configured to guide wire (340) along the length of guide tube assembly (330) as wire (340) translates within and relative to inner tube (334).

Lumen (333) is configured to receive a malleable member (350). Malleable member (350) is configured to provide malleability to inner tube (334). In some versions, the material that forms the outer region of inner tube (334) (including the material that defines lumens (331, 333, 335) is flexible and non-malleable, such that malleability of inner tube (334) is provided solely by malleable member (350). Malleable member (350) may include a malleable wire, rod, or tube. Malleable member (350) may additionally or alternatively include an articulation joint(s). All or a portion (e.g., between 0.3 cm and 2 inches) of malleable member (350) may comprise a material having low magnetic permeability, including by not limited to 316 stainless steel, nitinol, cobalt chromium, tungsten, PEEK, and polycarbonate, such that malleable member (350) will not interfere with any signals from wire (340). Various suitable materials and configurations that may be used to form malleable member (350) will be apparent to those of ordinary skill in the art in view of the teachings herein.

Figure 16:
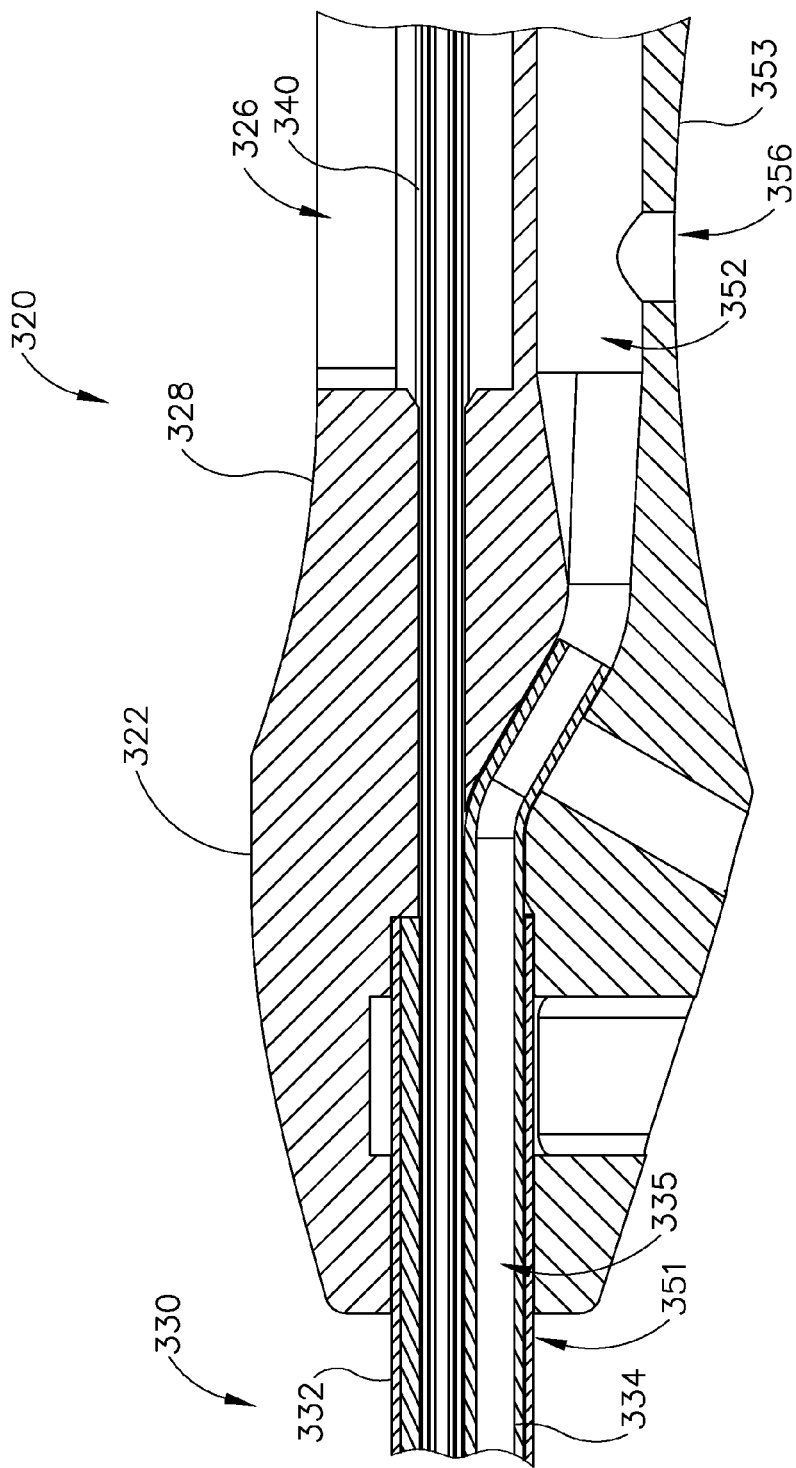
FIG. 16 depicts a detailed side cross-sectional view of the handle assembly of FIG. 14.
Figure 17:
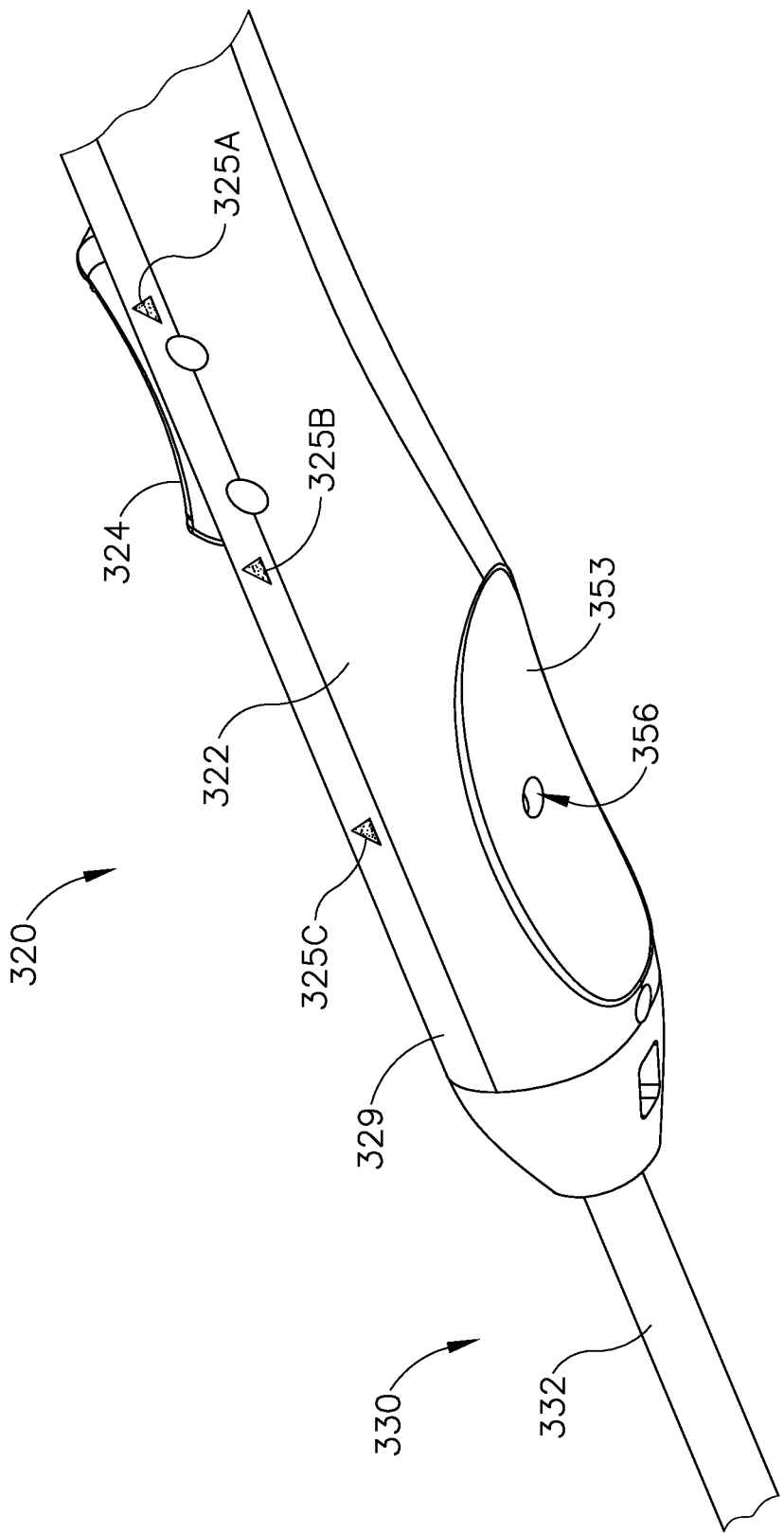
FIG. 17 depicts another detailed perspective view of the handle assembly of FIG. 14.

Lumen (335) is configured to provide suction to the distal end of inner tube (334) to remove blood, mucus, and other fluids from the surgical field. As shown in FIG. 16, lumen (335) is in fluid communication with a lumen (352) formed within body (322). A proximal end of lumen (352) of body (322) terminates in a luer port (354), which is best seen in FIGS. 10-11. A suction/vacuum source may be coupled with luer port (354) to provide suction to the distal end of inner tube (334). As best seen in FIGS. 16-17, body (322) further includes a suction port (356) that is in fluid communication with lumen (352) of body (322). The operator may control the suction provided to the distal end of inner tube (334) via lumen (335) by selectively covering or uncovering port (356) using his or her finger or thumb while simultaneously maneuvering device (320) and/or translating actuator (324). For instance, the operator may use his or her thumb to cover port (356) while simultaneously using his or her index finger to translate actuator (324). When port (356) is covered, the suction from the suction source may be fully delivered to the distal end of inner tube (334) via lumen (335). When port (356) is uncovered, the suction from suction source will be communicated through port (356) to the atmosphere, such that either no suction or just a limited amount of suction will travel further distally past port (356). In other words, the distal end of inner tube (334) receives full suction when port (356) is covered; and the distal end of inner tube (334) receives either no suction or just limited suction when port (356) is uncovered.

While port (356) is shown as being formed in a bottom surface (353) of body (322), it should be understood that port (356) may be provided at any other suitable location. For instance, port (356) may be located on actuator (324). As another merely illustrative example, port (356) may be located at a position on body (322) proximal to actuator (324). As yet another illustrative example, port (356) may be located at on a lateral side of body (322). Regardless of the particular location chosen for port (356), port (456) may be located at a position that will enable the operator to selectively cover/uncover port (356) while simultaneously operating actuator (324) with the same hand that is used to selectively cover/uncover port (356). Various suitable alternative locations and configurations for port (356) will be apparent to those of ordinary skill in the art in view of the teachings herein. It should also be understood that port (356) may be substituted with a footswitch actuated valve that is located upstream of luer port (354).

Wire (340) may be configured and operable substantially identically to wire (130) described above. Wire (340) of the present example comprises a flexible stacked-coil design. Wire (340) extends completely through body (322) and lumen (331) of inner tube (334). As mentioned above, wire (340) is configured to translate within and relative to inner tube (334) of guide tube assembly (330). Wire (340) is secured to actuator (324) such that translation of actuator (324) within slot (326) of body (322) causes concurrent translation of wire (340) relative to inner tube (334). This translation of wire (340) causes translation of a distal end (342) of wire (340) relative to guide tube assembly (330) as actuator (324) translates between the proximal longitudinal position, the intermediate longitudinal position, and the distal longitudinal position as described above and as will be described in more detail below.

The distal end (342) of wire (340) may be configured and operable substantially identically to distal end (132) of wire (130) described above. Distal end (342) of wire (340) of the present example is substantially straight and includes an atraumatic distal tip. As discussed above with reference to wire (130), distal end (342) of wire (340) may include a preformed bend (FIG. 4), a preformed curve (FIG. 5), or any other appropriate configuration. It should also be understood that the tip of distal end (342) may have any suitable configuration, including but not limited to a dome shape, a ball shape, a blueberry shape, or any other suitable shape.

Distal end (342) of wire (340) of the present example comprises a position sensor (345) and an ultrasound sensor (346). As will be described in more detail below, sensors (345, 346) enable distal end (342) of wire (340) to be used to provide mapping and/or navigation of the nasal cavity of a patient, passageways associated with the nasal cavity of a patient (e.g., paranasal sinus ostia and cavities, the frontal recess, the Eustachian tube, etc.), and/or other anatomical passageways (e.g., within the ear, nose, or throat, etc.). It should be understood that some variations of wire (340) may include position sensor (345) and omit ultrasound sensor (346). Some other variations of wire may include ultrasound sensor (346) and omit position sensor (345). In addition to or in lieu of having position sensor (345) and/or ultrasound sensor (346), distal end (342) of wire (340) may include a camera that is configured to provide real-time visualization of a surgical field.

In the present example, position sensor (345) includes a coil that is embedded within distal end (342) of wire (340) and that is in communication with one or more electrical conduits that extend along the length of wire (340). When position sensor (345) is positioned within an electromagnetic field (e.g., as generated by coils (202) of system (200)), movement of position sensor (345) within that magnetic field may generate electrical current in the coil, and this electrical current may be communicated along wire (340). This phenomenon may enable system (200) described above to determine the location of distal end (342) within a three dimensional space as will be described in greater detail below.

By way of example only, position sensor (345) and/or other components of wire (340) may be constructed and operable in accordance with at least some of the teachings of U.S. Pat. No. 8,702,626, the disclosure of which is incorporated by reference herein; U.S. Pat. No. 8,320,711, the disclosure of which is incorporated by reference herein; U.S. Pat. No. 8,190,389, the disclosure of which is incorporated by reference herein; U.S. Pat. No. 8,123,722, the disclosure of which is incorporated by reference herein; U.S. Pat. No. 7,720,521, the disclosure of which is incorporated by reference herein; U.S. Pat. Pub. No. 2014/0364725, now abandoned, the disclosure of which is incorporated by reference herein; U.S. Pat. Pub. No. 2014/0200444, now abandoned, the disclosure of which is incorporated by reference herein; U.S. Pat. Pub. No. 2012/0245456, issued as U.S. Pat. No. 9,198,736 on Dec. 1, 2015, the disclosure of which is incorporated by reference herein; U.S. Pat. Pub. No. 2011/0060214, now abandoned, the disclosure of which is incorporated by reference herein; U.S. Pat. Pub. No. 2008/0281156, issued as U.S. Pat. No. 9,167,961 on Oct. 27, 2015, the disclosure of which is incorporated by reference herein; and/or U.S. Pat. Pub. No. 2007/0208252, now abandoned, the disclosure of which is incorporated by reference herein. As another merely illustrative example, wire (340) may be constructed and operable in accordance with at least some of the teachings of U.S. Provisional Pat. App. No. 62/150,954, entitled "Guidewire with Navigation Sensor," filed on Apr. 22, 2015, the disclosure of which is incorporated by reference herein. Other suitable ways in which wire (340) may be constructed and operable will be apparent to those of ordinary skill in the art in view of the teachings herein.

Figure 18A:
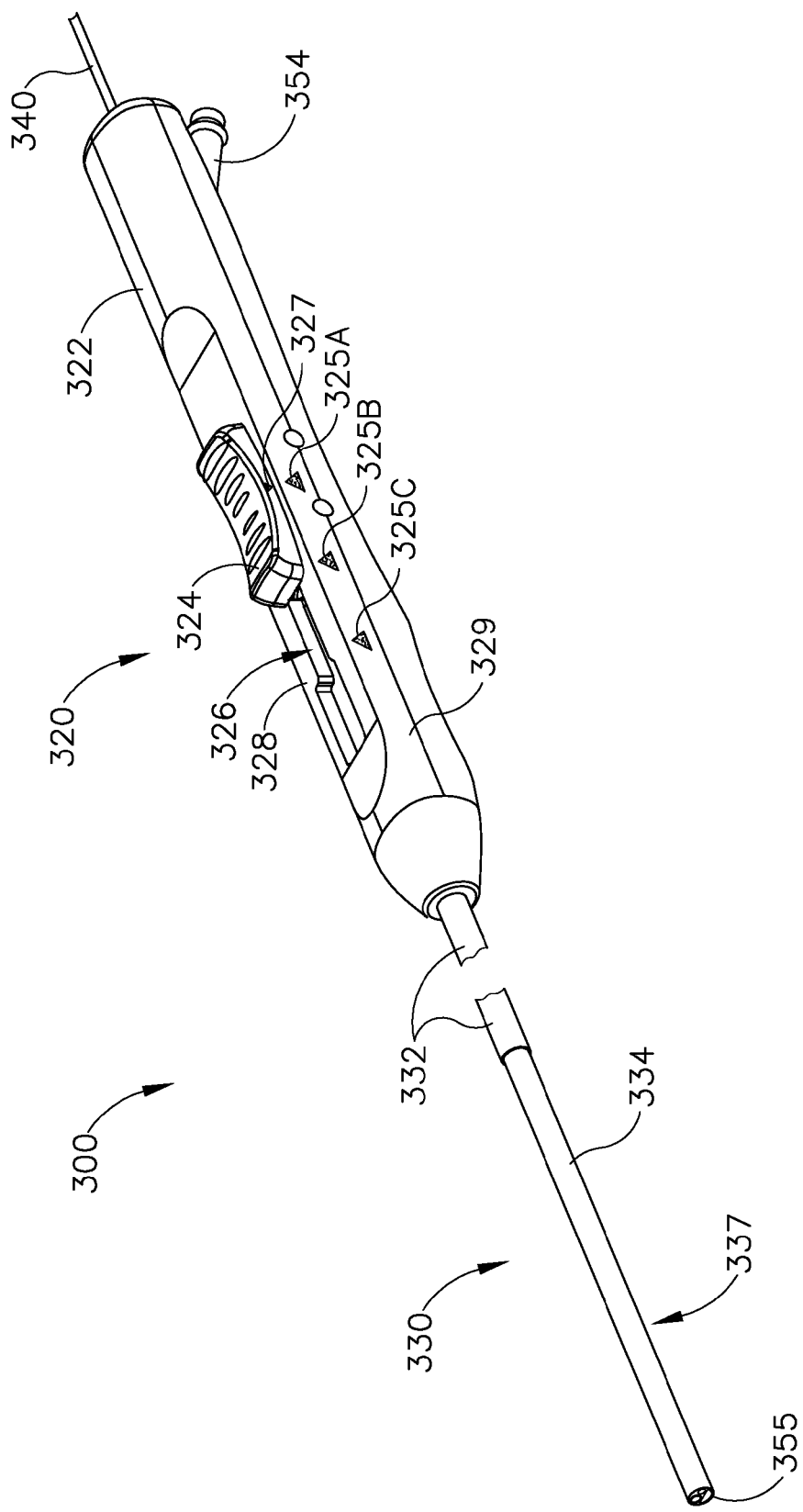
FIG. 18A depicts a perspective view of the device of FIG. 10, with a flexible wire of the device in a first longitudinal position.
Figure 18B:
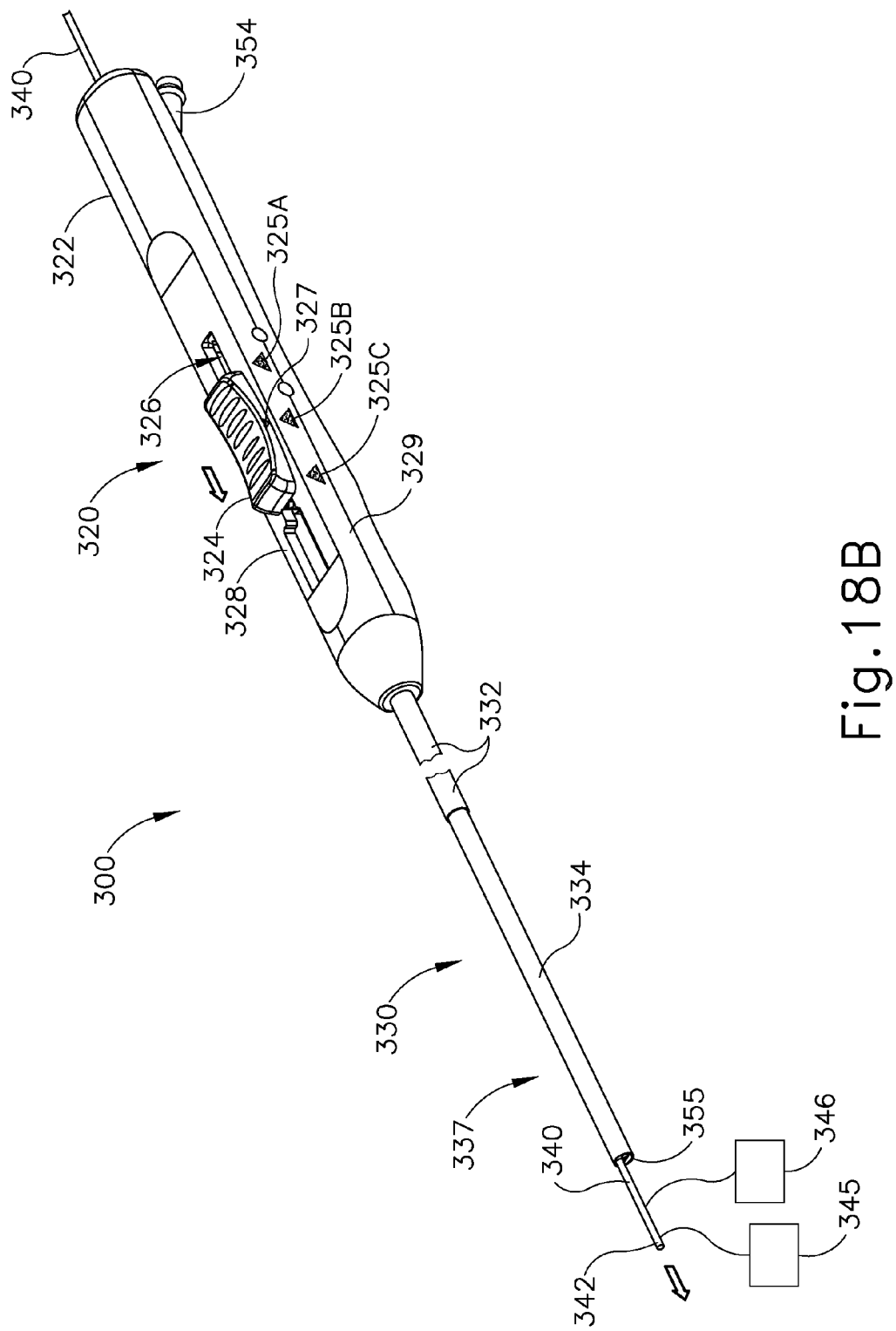
FIG. 18B depicts a perspective view of the device of FIG. 10, with the flexible wire of FIG. 18A moved to a second longitudinal position.
Figure 18C:
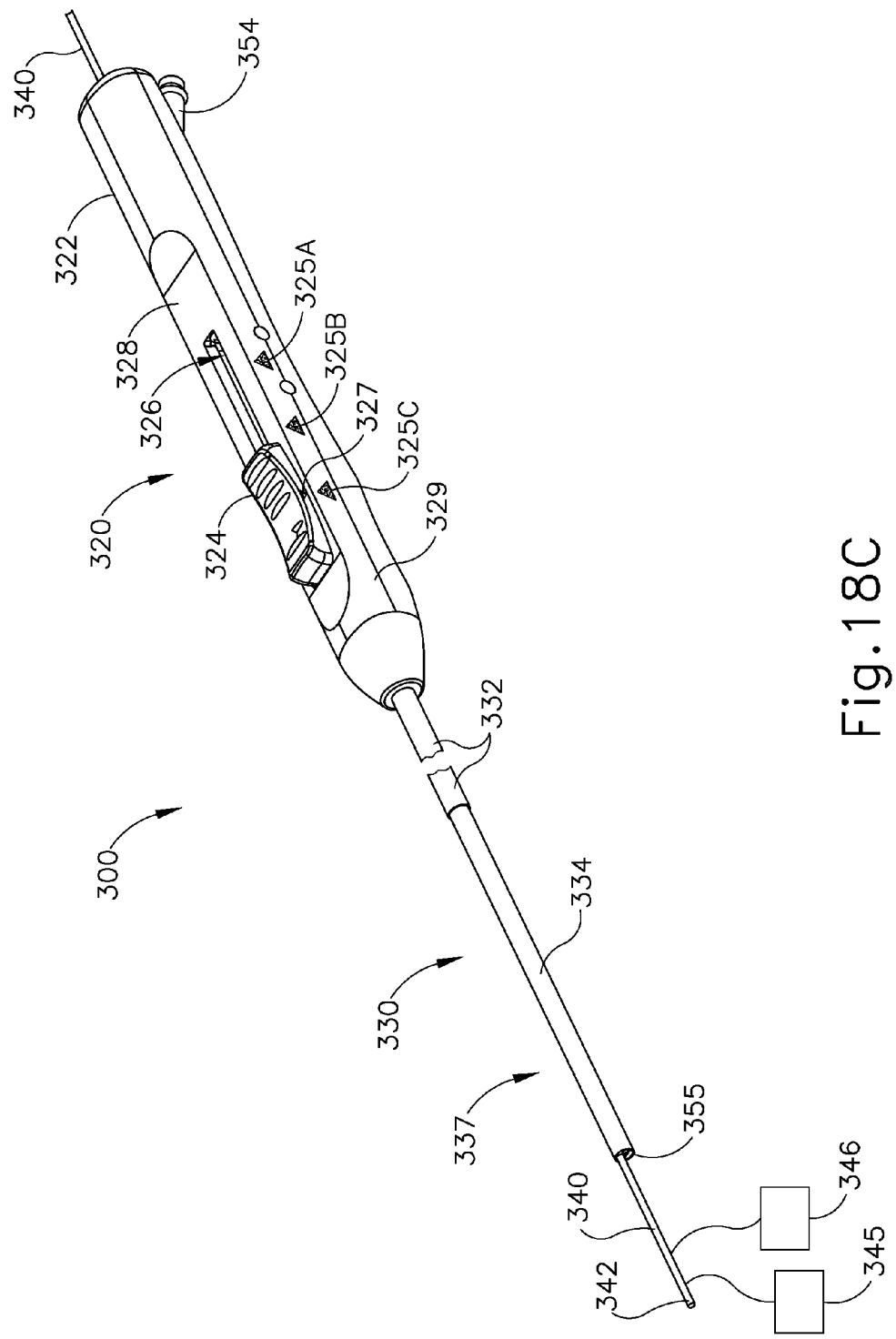
FIG. 18C depicts a perspective view of the device of FIG. 10, with the flexible wire of FIG. 18A moved to a third longitudinal position.

FIGS. 18A-18C show an exemplary method of operation of device (300). As shown in FIG. 18A, with actuator (324) in the proximal longitudinal position, the tip of distal end (342) of wire (340) is positioned flush with the distal edge (355) of inner tube (334). As actuator (324) is translated distally to the intermediate longitudinal position as shown in FIG. 18B, distal end (342) of wire (340) extends from the distal end of inner tube (334), such that at least a portion of distal end (342) is distal to distal edge (355) of inner tube (334). In some versions, the length of wire (340) that extends distally past distal edge (355) of inner tube (330) at this stage is between 0.5 cm and 1.5 cm. Alternatively, any other suitable length of wire (340) may extend distally past distal edge (355) of inner tube (334) at this stage. As actuator (324) is translated further distally to the distal longitudinal position as shown in FIG. 18C, distal end (342) of wire (340) extends further from the distal end of inner tube (334). In some versions, the length of wire (340) that extends distally past distal edge (355) of inner tube (334) at this stage is between 2 cm and 3.5 cm. Alternatively, any other suitable length of wire (340) may extend distally past distal edge (355) of inner tube (334) at this stage.

As described with reference to device (10), during use of device (300) in a patient, distal end (342) of wire (340) may contact one or more anatomical structures associated with the patient's paranasal sinuses and/or other anatomical structures (e.g., within the ear, nose, or throat, etc.). Wire (340) may have sufficient column strength to withstand buckling in response to longitudinally oriented forces when such contact occurs, at least when actuator (324) and wire (340) are in the intermediate longitudinal position shown in FIG. 18B. Wire (340) may additionally or alternatively be configured to buckle when such contact exceeds a threshold load. For instance, wire (340) may be configured to buckle when exposed to loads exceeding 7 Newtons of force, or any other appropriate force. It should also be understood that when actuator (324) and wire (340) are in the intermediate longitudinal position shown in FIG. 18B or in the distal longitudinal position shown in FIG. 18C, the length of wire (340) that is extended distally of distal edge (355) allows distal end (342) to deflect laterally when distal end (342) contacts one or more anatomical structures associated with the patient's paranasal sinuses and/or other anatomical structures. This may be useful when distal end (342) contacts a particularly fragile anatomical structure. In other words, the flexibility provided by wire (340) may prevent distal end (342) from inadvertently fracturing a fragile anatomical structure as distal end (342) is pushed against the fragile anatomical structure during a process of mapping or navigation as described herein.

It should be understood from the foregoing that device (300) may be provided in three different modes based on the longitudinal position of actuator (324) and wire (340). When actuator (324) and wire (340) are in the proximal position shown in FIG. 18A, device (300) is in a rigid mode. In the rigid mode, wire (340) does not provide any flexibility as distal end (342) contacts anatomical structures. When actuator (324) and wire (340) are in the intermediate position shown in FIG. 18B, device (300) is in a flexible mode. In the flexible mode, wire (340) provides an intermediate amount of "give" or flexibility as distal end (342) contacts anatomical structures. In some versions, distal end (342) of wire (340) is between approximately 0.5 cm and approximately 1.5 cm distal to distal edge (355) of inner tube (334) when device (300) is in the flexible mode shown in FIG. 18B. When actuator (324) and wire (340) are in the distal position shown in FIG. 18C, device (300) is in an extended mode. In the extended mode, wire (340) provides the most "give" or flexibility as distal end (342) contacts anatomical structures. By way of example only, wire (340) may be advanced to a longitudinal position where distal end (342) is approximately 2.0 cm, approximately 2.5 cm, approximately 3.0 cm, or up to approximately 3.5 cm distal to distal edge (355) of inner tube (334).

Device (300) may be used with system (200) described above. Device (300) would be used to gently probe anatomical structures with distal end (342) of wire (340). This would allow for identification of anatomical structures that cannot be directly visualized endoscopically or anatomical structures that are outside of an endoscopic view using position sensor (345) and/or ultrasonic sensor (346) as described above with reference to device (10) and system (200). Device (300) could be used to identify any portion of the anatomy, including structures and spaces within the nasal cavity of a patient (e.g., paranasal sinus ostia and cavities, the frontal recess, the Eustachian tube, etc.), and/or other anatomical passageways (e.g., within the ear, nose, or throat, etc.) via gentle probing to prevent damage any such anatomic structures. Distal end (342) of wire (340) thus can identify structures and the navigation software of system (200) could use this location information to generate a computer-rendered 3-D image via display (216) as described above. Device (300) may also be used to provide suction to remove blood, mucus, and other fluids from the surgical field. With wire (340) in the retracted position, device (300) may be used as a standard navigable probe and/or as a simple suction device.

After device (300) is used in a patient, device (300) may be sterilized for further use. Alternatively, device (300) may be discarded after a single use.

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a handle assembly, wherein the handle assembly comprises: (i) a body, and (ii) an actuator; (b) a guide tube extending distally from the handle assembly, wherein the guide tube has a distal end; (c) a wire slidably disposed in the guide tube, wherein the wire has a distal end including a sensor, wherein the sensor is configured to cooperate with a navigation system to generate a map of anatomical structures within a patient, wherein the wire is coupled with the actuator, wherein the actuator is movable relative to the body to move the wire relative to the guide tube.

Example 2

The apparatus of Example 1 or any of the following Examples, wherein the handle assembly further comprises a cable extending from the body.

Example 3

The apparatus of Example 2, wherein the cable is coupled with a navigation system to communicate signals from the sensor to the navigation system.

Example 4

The apparatus of any of Examples 1 through 3, wherein the handle assembly further comprises a cartridge, wherein the cartridge is configured to removably couple with the body.

Example 5

The apparatus of Example 4, wherein the actuator is integrated into the cartridge such that the actuator is removable from the body.

Example 6

The apparatus of any of Examples 4 through 5, wherein the wire is integral with the cartridge such that the wire is removable from the guide tube as the cartridge is removed from the body.

Example 7

The apparatus of any of Examples 1 through 6, wherein the guide tube is integral with the body.

Example 8

The apparatus of any of Examples 1 through 7, wherein the guide tube is rigid.

Example 9

The apparatus of Example 8, wherein the guide tube has a distal region with a preformed bend.

Example 10

The apparatus of any of Examples 1 through 9, wherein at least a distal portion of the guide tube is malleable.

Example 11

The apparatus of any of Examples 1 through 10, wherein a distal portion of the wire includes a preformed bend.

Example 12

The apparatus of Example 11, wherein the preformed bend defines an angle with a vertex.

Example 13

The apparatus of Example 11, wherein the preformed bend defines a curve.

Example 14

The apparatus of any of Examples 1 through 13, wherein the wire has a distal end with a ball tip.

Example 15

The apparatus of Example 14, wherein the sensor is integrated into the ball tip.

Example 16

The apparatus of any of Examples 1 through 15, wherein the sensor comprises a coil.

Example 17

The apparatus of Example 16, wherein the coil is responsive to movement of the distal end of the wire in an electromagnetic field.

Example 18

The apparatus of any of Examples 1 through 17, wherein the actuator is configured to drive the wire between a proximal position relative to the guide tube and a distal position relative to the guide tube, wherein the distal end of the wire is flush with the distal end of the guide tube when the wire is in the proximal position, wherein the distal end of the wire is distal to the distal end of the guide tube when the wire is in the distal position.

Example 19

The apparatus of Example 18, wherein the handle assembly provides a plurality of position indicators, wherein the position indicators comprise a first indicator and a second indicator, wherein the first indicator is associated with the proximal position, wherein the second indicator is associated with the distal position.

Example 20

The apparatus of Example 19, wherein the indicators comprise visual indicators.

Example 21

The apparatus of any of Examples 19 through 20, wherein the indicators comprise tactile feedback features.

Example 22

The apparatus of Example 21, wherein the tactile feedback features comprise detent structures.

Example 23

The apparatus of Example 19, wherein the indicators further comprise a third indicator, wherein the third indicator is associated with the actuator and the wire being located in an intermediate position, wherein the intermediate position is positioned between the distal position and the proximal position.

Example 24

The apparatus of any of Examples 1 through 23, wherein the wire forms a service loop within the handle assembly.

Example 25

The apparatus of Example 24, wherein a proximal portion of the wire is fixedly secured relative to the handle assembly, wherein the service loop is configured to permit a distal portion of the wire to translate relative to the handle assembly while the proximal portion of the wire remains fixedly secured relative to the handle assembly.

Example 26

The apparatus of any of Examples 1 through 25, wherein the wire is rotatable within the guide tube.

Example 27

The apparatus of Example 26, wherein the actuator comprises a rotatable member operable to rotate the wire within the guide tube.

Example 28

An apparatus comprising: (a) a handle assembly, wherein the handle assembly comprises: (i) a body, and (ii) an actuator; (b) a guide tube assembly extending distally from the handle assembly, wherein the guide tube assembly comprises a rigid member and a malleable member; (c) a wire slidably disposed in the guide tube assembly, wherein the wire has a distal end including a sensor, wherein the sensor is configured to cooperate with a navigation system to provide image guided navigation of anatomical structures within a patient, wherein the wire is coupled with the actuator, wherein the actuator is movable relative to the body to move the wire relative to the guide tube.

Example 29

The apparatus of Example 28, wherein the malleable member comprises an inner tube, wherein the rigid member comprises an outer sheath.

Example 30

The apparatus of any of Examples 28 through 29, wherein the malleable member extends distally from the rigid member.

Example 31

The apparatus of any Examples 28 through 30, wherein the malleable member comprises at least one lumen.

Example 32

The apparatus of Example 31, wherein the wire is slidably disposed within a lumen of the at least one lumens of the malleable member.

Example 33

The apparatus of any of Examples 31 through 32, wherein the malleable member comprises a flexible portion and a malleable portion, wherein the flexible portion defines a lumen of the at least one lumens of the malleable member, wherein the malleable portion is disposed the lumen defined by the flexible portion.

Example 34

The apparatus of any of Examples 31 through 33, wherein a lumen of the at least one lumens of the malleable member is configured to provide suction to a distal end of the malleable member.

Example 35

The apparatus of Example 34, wherein the body comprises a luer port in fluid communication with the lumen configured to provide suction to the distal end of the malleable inner member.

Example 36

The apparatus of any of Examples 28 through 35, wherein the rigid member is substantially straight.

Example 37

The apparatus of any of Examples 28 through 36, wherein the rigid member includes a preformed bend.

Example 38

The apparatus of Example 37, wherein the preformed bend defines an angle with a vertex.

Example 39

The apparatus of Example 37, wherein the preformed bend defines a curve.

Example 40

The apparatus of any of Examples 28 through 39, wherein the wire has a distal end with a ball tip.

Example 41

The apparatus of Example 40, wherein the sensor is integrated into the ball tip.

Example 42

The apparatus of any of Examples 28 through 41, wherein the sensor comprises a coil.

Example 43

The apparatus of Example 42, wherein the coil is responsive to movement of the distal end of the wire in an electromagnetic field.

Example 44

The apparatus of any Examples 28 through 43, wherein the actuator is configured to drive the wire between a proximal position relative to the guide tube assembly and a distal position relative to the guide tube assembly, wherein the distal end of the wire is flush with the distal end of the guide tube assembly when the wire is in the proximal position, wherein the distal end of the wire is distal to the distal end of the guide tube assembly when the wire is in the distal position.

Example 45

The apparatus of Example 44, wherein the handle assembly provides a plurality of position indicators, wherein the position indicators comprise a first indicator and a second indicator, wherein the first indicator is associated with the proximal position, wherein the second indicator is associated with the distal position.

Example 46

The apparatus of Example 45, wherein the indicators comprise visual indicators.

Example 47

The apparatus of Example 45, wherein the indicators comprise tactile feedback features.

Example 48

The apparatus of Example 47, wherein the tactile feedback features comprise detent structures.

Example 49

The apparatus of Example 45, wherein the indicators further comprise a third indicator, wherein the third indicator is associated with the actuator and the wire being located in an intermediate position, wherein the intermediate position is positioned between the distal position and the proximal position.

Example 50

The apparatus of any of Examples 28 through 49, wherein the actuator comprises a rotatable member operable to rotate the wire within the guide tube assembly.

Example 51

A method of using an apparatus, wherein the apparatus comprises: (a) a handle assembly, wherein the handle assembly comprises: (i) a body, and (ii) an actuator; (b) a guide tube extending distally from the handle assembly, wherein the guide tube has a distal end; and (c) a wire slidably disposed in the guide tube, wherein the wire has a distal end including a sensor, wherein the sensor is configured to cooperate with a navigation system to generate a map of anatomical structures within a patient, wherein the wire is coupled with the actuator, wherein the actuator is movable relative to the body to move the wire relative to the guide tube; wherein the method comprises: (a) inserting a distal end of the guide tube through a nostril of a patient; (b) actuating the actuator to drive the wire relative to the guide tube such that the distal end of the wire is located distal to the distal end of the guide tube; and (c) using the distal end of the wire in conjunction with a navigation system to map anatomical structures within the nasal cavity of the patient.

VI. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/ replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a handle assembly, wherein the handle assembly comprises
      (i) a body,
      (ii) a cable configured to communicate an electrical signal to a navigation system, and
      (iii) a first portion of an adapter coupled with a distal end of the cable;
   (b) a guide tube extending distally from the handle assembly, wherein the guide tube has a distal end; and
   (c) a cartridge assembly configured to be removably coupled with the handle assembly, wherein the cartridge assembly includes:
      (i) an actuator, wherein the actuator is movable relative to the body to move the wire relative to the guide tube, and
      (ii) a wire coupled with the actuator and configured to communicate an electrical signal to the cable, wherein the wire is slidably disposed in the guide tube, wherein the wire includes:
         (A) a distal end including a sensor, wherein the distal end of the wire is configured to translate relative to the body,
         (B) a proximal end that terminates at a second portion of the adapter, wherein the second portion of the adapter is configured to be removably coupled with the first portion of the adapter, wherein the proximal end is fixed relative to the body, and
         (C) an intermediate portion configured to gather within the body as a service loop to provide freedom of movement of the distal end of the wire relative to the body as the distal end of the wire translates proximally relative to the body,
      wherein the sensor is configured to cooperate with the navigation system to generate a map of anatomical structures within a patient.

2. The apparatus of claim 1, wherein the guide tube is rigid.

3. The apparatus of claim 2, wherein the guide tube has a distal region with a preformed bend.

4. The apparatus of claim 1, wherein at least a distal portion of the guide tube is malleable.

5. The apparatus of claim 1, wherein the distal end of the wire has a rounded tip.

6. The apparatus of claim 5, wherein the sensor is integrated into the rounded tip.

7. The apparatus of claim 1, wherein the sensor comprises a coil, wherein the coil is responsive to movement of the distal end of the wire in an electromagnetic field.

8. The apparatus of claim 1, wherein the actuator is configured to drive the wire between a proximal position relative to the guide tube and a distal position relative to the guide tube, wherein the distal end of the wire is flush with the distal end of the guide tube when the wire is in the proximal position, wherein the distal end of the wire is distal to the distal end of the guide tube when the wire is in the distal position.

9. The apparatus of claim 8, wherein the handle assembly provides a plurality of position indicators, wherein the position indicators comprise a first indicator and a second indicator, wherein the first indicator is associated with the proximal position, wherein the second indicator is associated with the distal position.

10. The apparatus of claim 9, wherein the indicators comprise tactile feedback features, wherein the tactile feedback features comprise detent structures.

11. An apparatus comprising:
(a) a handle assembly, wherein the handle assembly comprises:
   (i) a body, and
   (ii) a cable configured to communicate an electrical signal to a navigation system;
(b) a guide tube assembly extending distally from the handle assembly, wherein the guide tube assembly comprises a rigid member and a malleable member; and
(c) a cartridge assembly configured to be removably coupled with the handle assembly, wherein the cartridge assembly includes:
   (i) an actuator that includes a rotatable member, and
   (ii) a wire configured to communicate an electrical signal to the cable, wherein the wire is slidably disposed in the guide tube assembly, wherein the wire includes:
      (A) a proximal end,
      (B) a distal end including a sensor, wherein the sensor is configured to cooperate with the navigation system to provide image guided navigation of anatomical structures within a patient, wherein the wire is coupled with the actuator, wherein the actuator is movable relative to the body to move the distal end of the wire relative to the guide tube such that the proximal end of the wire is configured to remain fixed relative to the body while the distal end of the wire moves in response to movement of the actuator, wherein the rotatable member is mechanically coupled with the wire such that rotation of the rotatable member about a longitudinal axis of the rotatable member causes concurrent rotation of the wire about a longitudinal axis of the wire, and
      (C) an intermediate portion positioned and configured to gather within the body as a service loop to provide freedom of movement of the distal end relative to the body while the proximal end remains fixed relative to body.

12. The apparatus of claim 11, wherein the malleable member comprises an inner tube, wherein the rigid member comprises an outer sheath.

13. The apparatus of claim 11, wherein the malleable member comprises a first lumen, wherein the wire is slidably disposed within the first lumen of the malleable member.

14. The apparatus of claim 13, wherein the malleable member further comprises a second lumen that is configured to provide suction to a distal end of the malleable member.

15. A method of using an apparatus, wherein the apparatus comprises:
(a) a handle assembly, wherein the handle assembly comprises:
   (i) a body,
   (ii) a cable configured to communicate an electrical signal to a navigation system, and
   (iii) a first portion of an adapter coupled with a distal end of the cable;
(b) a guide tube extending distally from the handle assembly, wherein the guide tube has a distal end; and
(c) a cartridge assembly configured to be removably coupled with the handle assembly, wherein the cartridge assembly includes:
   (i) an actuator, wherein the actuator is movable relative to the body to move the wire relative to the guide tube, and
   (ii) a wire coupled with the actuator and configured to communicate an electrical signal to the cable, wherein the wire is slidably disposed in the guide tube, wherein the wire includes a proximal end, a distal end, and an intermediate portion disposed between the proximal and distal ends of the wire, wherein the proximal end terminates at a second portion of the adapter, wherein the intermediate portion includes a service loop configured to provide freedom of movement of the distal end of the wire relative to the body, wherein the distal end of the wire includes a sensor, wherein the sensor is configured to cooperate with the navigation system to generate a map of anatomical structures within a patient, wherein the wire is coupled with the actuator;
wherein the method comprises:
(a) providing the handle assembly and the cartridge assembly separate from one another;
(b) coupling the first and second portions of the adapter together to couple the cable of the handle assembly with the wire of the cartridge assembly together;
(c) inserting a distal end of the guide tube through a nostril of the patient;
(d) actuating the actuator to drive the wire relative to the guide tube such that the distal end of the wire moves distal to the distal end of the guide tube while the proximal end of the wire remains fixed to the second portion of the adapter and while the service loop of the intermediate portion decreases in size as the distal end of the wire moves distally; and
(e) using the distal end of the wire in conjunction with the navigation system to map anatomical structures within the nasal cavity of the patient.

16. The apparatus of claim 1, wherein the cartridge assembly includes a housing, wherein the housing of the cartridge assembly and the body of the handle assembly fully surround the proximal end of the wire.

17. The apparatus of claim 1, wherein the cartridge assembly is configured to be coupled within an opening of the handle assembly using a snap-fit, an interference-fit, or a friction-fit.

18. The apparatus of claim 17, wherein at least one of the cartridge assembly or handle assembly includes latches, clasps, or clamps configured to releasably secure the cartridge assembly relative to the handle assembly.

19. The apparatus of claim 11, wherein the rotatable member and the wire are coupled together using at least one of a gear, a cable, or a belt.

20. The method of claim 15, wherein the actuator includes a rotatable member that is mechanically coupled with the wire, wherein the method further comprises rotating the rotatable member about a longitudinal axis of the rotatable member to rotate the wire about a longitudinal axis of wire.

\* \* \* \* \*